US010150970B2

(12) United States Patent
Howard et al.

(10) Patent No.: US 10,150,970 B2
(45) Date of Patent: Dec. 11, 2018

(54) METHODS TO INCREASE ANTIGENICITY OF MEMBRANE-BOUND POLYPEPTIDES PRODUCED IN PLANTS

(71) Applicant: Applied Biotechnology Institute, Inc., San Luis Obispo, CA (US)

(72) Inventors: John Howard, Cayucos, CA (US); Celine Hayden, San Luis Obispo, CA (US); Rafael Jimenez-Flores, San Luis Obispo, CA (US)

(73) Assignee: Applied Biotechnology Institute, Inc., San Luis Obsipo, CA (US)

(*) Notice: Subject to any disclaimer, the term of this patent is extended or adjusted under 35 U.S.C. 154(b) by 914 days.

(21) Appl. No.: 14/198,712

(22) Filed: Mar. 6, 2014

(65) Prior Publication Data

US 2014/0205625 A1    Jul. 24, 2014

Related U.S. Application Data

(63) Continuation-in-part of application No. 13/558,874, filed on Jul. 26, 2012, now abandoned.

(60) Provisional application No. 61/512,351, filed on Jul. 27, 2011.

(51) Int. Cl.
| | | |
|---|---|---|
| *C12N 15/82* | (2006.01) | |
| *A61K 39/12* | (2006.01) | |
| *A61K 39/21* | (2006.01) | |
| *A61K 39/29* | (2006.01) | |
| *A61K 39/00* | (2006.01) | |

(52) U.S. Cl.
CPC .......... *C12N 15/8257* (2013.01); *A61K 39/12* (2013.01); *A61K 39/21* (2013.01); *A61K 39/292* (2013.01); *C12N 15/8258* (2013.01); *A61K 2039/517* (2013.01); *A61K 2039/542* (2013.01); *A61K 2039/545* (2013.01); *A61K 2039/55544* (2013.01); *C12N 2740/16034* (2013.01)

(58) Field of Classification Search
None
See application file for complete search history.

(56) References Cited

U.S. PATENT DOCUMENTS

| | | | |
|---|---|---|---|
| 4,466,923 A * | 8/1984 | Friedrich | ........... B01D 11/0203 554/11 |
| 4,493,854 A | 1/1985 | Eldridge | |
| 4,675,198 A | 6/1987 | Sevenants | |
| 5,120,558 A | 6/1992 | Dietmar | |
| 5,252,729 A | 10/1993 | DeCrosta | |
| 5,484,719 A | 1/1996 | Lam | |
| 5,612,487 A | 3/1997 | Lam | |
| 5,629,175 A | 5/1997 | Goodman | |
| 5,654,184 A | 8/1997 | Curtiss | |
| 5,679,880 A | 10/1997 | Curtiss | |
| 5,686,079 A | 11/1997 | Curtiss | |
| 5,753,296 A * | 5/1998 | Girsh | ...................... A23G 1/02 426/425 |
| 5,824,870 A | 10/1998 | Baszczynski | |
| 5,914,123 A | 6/1999 | Arntzen | |
| 6,087,558 A | 1/2000 | Howard | |
| 6,034,298 A | 3/2000 | Lam | |
| 6,136,320 A | 10/2000 | Arntzen | |
| 6,504,085 B1 | 1/2003 | Howard | |
| 7,179,961 B2 | 2/2007 | Howard | |
| 2003/0223964 A1 | 12/2003 | Barnett | |
| 2004/0040061 A1 | 2/2004 | Horn | |

FOREIGN PATENT DOCUMENTS

| | | |
|---|---|---|
| WO | WO9118618 A1 | 12/1991 |
| WO | WO9954452 A1 | 10/1999 |

OTHER PUBLICATIONS

Shah et al (Archives of Biochemistry and Biophysics, 2015, 588: 41-49).*
Mariod et al (Journal of the American Oil Chemists' Society, 2011, 88(7): 931-935).*
Wang et al (Eur. J. Lipid Sci. Technol., 2007, 109: 567-574).*
Desombere et al (J. Virol., 2006 80(7): 3506-3514).*
Elkholy et al (Arab J. Biotech., 2009, 12(2): 291-302).*
Kong et al (PNAS, 2001, 98(20): 11539-11544).*
Freidrich et al (JAOCS, 1984, 61(2): 223-228).*
Moreau et al (JAOCS, 2003, 80(11): 1063-1067;).*
Bahrami et al (J. Sci. Food Agric., 2014, 94(3): 415-423).*
Gavilanes et al (Biochem J., 1990, 265: 857-864).*
Brunner (Journal of Food Engineering, 2005, 67: 21-33;).*
Ronyai et al (Journal of Supercritical Fluids, 1998, 14: 75-81).*
Tacket et al (Vaccine, 2004, 22: 4385-4389).*
Herrero et al (Journal of Chromatography A, 2010, 1217: 2495-2511).*
Mohamed et al. "Extraction Technology in Food Processing" Food Technology Magazine Jun. 2002, The World Markets Research Centre, London, UK.

(Continued)

*Primary Examiner* — Stephen Uyeno
(74) *Attorney, Agent, or Firm* — McKee, Voorhees & Sease, PLC

(57) ABSTRACT

Increased antigenicity of a membrane-bound polypeptide produced from a plant is provided in a process in which extraction of the polypeptide or other compounds from the plant is such that phospholipids are associated with the polypeptide. Reducing fat by supercritical fluid extraction increases antigenicity of such plant-produced membrane-bound polypeptides. Methods and means of producing such membrane-bound polypeptides are provided. Methods to produce a protective response in animals are provided by administering to the animal the membrane-bound polypeptide. Binding of antibody specific to the membrane-bound polypeptide is increased. The process provides for increased preferred formation of the membrane-bound polypeptide. Stability of the membrane-bound polypeptide is increased when the plant material is defatted.

13 Claims, 12 Drawing Sheets

Specification includes a Sequence Listing.

(56) References Cited

OTHER PUBLICATIONS

Brunner (2005) "Supercritical fluids: technology and application to food processing" Journal of Food Engineering, 67, 21-33.
Mason et al. (1998) Vaccine 16:13361343.
Wigdorovitz et al. (1999) Virology 255:347-353.
Kaputsa et al. (1999) FASEB J. 13:1796-1799.
Streatfield et al. (2001) "Plant based vaccines—unique advances" Vaccine 19:2742-2748.
Thanavala et al. (1995) Proc. Natl. Acad. Sci. U.S.A. 92:3358-3361.
Mason et al., (1996) Proc. Natl. Acad. Sci. 93:5335-5340.
Fischer et al. "Molecular farming of pharmaceutical plroteins" Transgenic Research, vol. 9, pp. 279-299 (2000).
Eshagi et al., "An efficient strategy for high-throughput expression screening of recombinant integral membrane proteins" Protein Science, 14:676-683 (2005).
Aucouturier et al. (2006) Vaccine vol. 24, Supp. 2 pp. S44-S45 (International Workshop on Vaccine Adjuvants and Glycoconjugates, Varadero, Cuba Apr. 11-15, 2004).
Grisshammer (2006) Current Opinion in Biotechnology 17:337-340.
Lomonossoff et al. "Cowpea mosaic virus-based vaccines" Curr. Top. Microbial. Immunol. 240, 177-189 (1999).
Hayden et al. "Bioencapsulation of the hepatitis B surface antigen and its use as an effective oral immunogen" vol. 30, Vaccine, Issue 19 (Apr. 19, 2012).
Horn et al. Appeal decision U.S. Appl. No. 10/375,657, Publication No. 20040040061 Sep. 13, 2011.
Horn et al. "Expression of an SIV protein in transgenic maize for use as an edible vaccine and reagent supply" HIV-1 Protection and control by vaccination, Apr. 5-10 Keystone, CO; Workshop 1 Vaccine Innovation and New Investigators, 2002 Keystone meeting Tuesday Apr. 9, 2002 Presentation and Poster (P#216). Also presented at Fifth Annual Conference on Vaccine Research May 6-8, 2002, Baltimore, MD (#P11); also at 10th IAPTC&B Congress, Jun. 23-28, 2002, Orlando, FL (#P-1154).
Zhang et al., "In planta expression of HIV-1p24 protein using an RNA plant virus-based expression vector," Molecular Biology vol. 14, Feb. 2000, abstract and article.
Durrani et al. "Intranasal immunization with a plant virus expressing a peptide from HIV-1 gp41 stimulates better mucosal and systemic HIV-1 specific IgA and IgG than orla immunization" Journal of Immunological Methods 220 (1998) 93-103.
Yushbov et al. "Antigens produced in plants by infection with chimeric plant viruses immunized against rabies virus and HIV-1" Proc. Natl. Acad. Sci. USA vol. 94, 5784-5788, May 1997.
Chargelegue et al. "Design and characterization of recombinent antigens and antibodies engineered in transgenic plants" Immunology, vol. 98, No. Supp.1, p. 128 (Dec. 1999).
Mossman et al. "Protection against lethan simian immunodeficiency virus SIV-smmPBj14 disease by a recombinant Semiliki Forest Virus gp160 vaccine and by a gp120 busunit vaccine" Journal of Virology vol. 70, pp. 1953-1960 (1996).
Ma et al. (1999) "Plant expression systems for the production of vaccines" Curr. Top Microbiol. Immuno. 236, 175-292.
Horvath et al. "The production of recombinant proteins in transgenic barley grains" PNAS vol. 97, pp. 1914-1919 (2000).
Jensen "Transgenic barley expressing a protein-engineered, thermostable (1,3-1,4) beta-glucanase during germination" PNAS vol. 93, pp. 3487-3491 (1996).
Wichukchina et al. "Transformation of HIV-1 Envelope glycoprotein 120 in tobacco plant" Kasetsart J. (Nat. Sci.) 40:96-101 (2006).
Hayden (2012) "Production of highly concentrated, heat-stable hepatitis B surface antigen in maize" Plant Biotechnology Journal 10, 979-984.
List et al. (1989) "Oxidative Stability of Seed Oils Extracted with Supercritical Carbon Dioxide" JAOCS, vol. 66, No. 1 pp. 98-101.
Froning et al. (1990) "Extraction of Cholesterol and Other Lipids from Dried Egg Yolk Using Supercritical Carbon Dioxide" Journal of Food Science vol. 55, No. 1, pp. 95-98.
Christianson et al. (1984) "Supercritical Fluid Extraction of Dry-Milled Corn Germ with Carbon Dioxide" Journal of Food Science vol. 49 pp. 229-232.
Frederich et al. (1982) "Characterization of Soybean Oil Extracted by Supercritical Carbon Dioxide and Hexane" J. Agric. Food Chem. 30, pp. 192-193.
Moreau et al, (2003) "Pressurized liquid extraction of polar and nonpolar lipids in corn and oats with hexane, methylene chloride, isopropanol and ethanol" JAOCS, vol. 80, No. 11 pp. 1063-1066.
Matthaus et al. (2001) "Comparison of Different Methods for the Determination of the Oil Content in Oilseeds" JAOCS, vol. 78, No. 1 pp. 95-102.
Hayden et al. (2014) "Supercritical fluid extraction provides an enhancement to the immune response for orally-delivered hepatitis B surface antigen" Vaccine 32, 1240-1246.
Hayden et al. (2014) "Bioencapsulation of the hepatitis B surface antigen and its use as an effective oral immunogen" Vaccine 30, 2937-2942.
"Membrane proteins of known 3D structure", http://blanco.biomol.uci.edu/mpstruc/listAll/list, Stephen White laboratory, UC Irvine, last modified Mar. 8, 2013 and accessed by Applicant Mar. 11, 2013.

\* cited by examiner

```
     ATGGCCAAC AAGCACCTGA GCCTCTCCCT CTTCCTCGTG CTCCTCGGCC
 51  TCTCCGCCTC CCTCGCCAGC GGCGAGTCCA CCACCTCCGG CTTCCTCGGC
101  CCGCTCCTCG TGCTCCAGGC CGGCTTCTCC CTCCTCACCC GCATCCTCAC
151  CATCCCGCAG TCCCTCGACT CCTGGTGGAC CTCCCTCAAC TTCCTCGGCG
201  GCGCCCCGAC CTGCCCGGGC CAGAACCTCC AGTCCCCGAC CTCCAACCAC
251  TCCCCGACCT CCTGCCCGCC CACCTGCCCG GCTACCGCT GGATGTGCCT
301  CCGCCGCTTC ATCATCTTCC TCTTCATCCT CCTGCTCTGC CTCATCTTCC
351  TCCTCGTGCT CGTGGACTAC CAGGGCATGC TCCCGGTGTG CCCGCTCCTC
401  CCGGGCACCT CCACGACCTC CACCGGCCCG TGCAAGACCT GCACCATCCC
451  GGCCCAGGGC ACCTCCATGT TCCCGTCCTG CTGCTGCACC AAGCCGTCCG
501  ACGGCAACTG CGCCTGCATC CCGATCCCGT CCTCCTGGGC CTTCGCCCGC
551  TTCCTCTGGG AGTGGGCCTC CGTGCGCTTC TCCTGGCTCT CCCTCCTCGT
601  GCCGTTCGTG CAGTGGTTCG TGGGCCTCTC CCCGACCGTG TGGCTCTCCG
651  TGATCTGGAT GATGTGGTAC TGGGGCCCGT CCCTCTACAA CATCCTCTCC
701  CCGTTCCTCC CGCTCCTCCC GATCTTCTTC TGCCTCTGGG TGTACATCTGA
751  A
```

Figure 1

```
   1 aagcttgccg agtgccatcc ttggacactc gataaagtat attttatttt ttttattttg
  61 ccaaccaaac ttttgtggt atgttcctac actatgtaga tctacatgta ccattttggc
 121 acaattacat atttacaaaa atgttttcta taaatattag atttagttcg tttatttgaa
 181 tttcttcgga aaattcacat ttaaactgca agtcactcga acatggaaa accgtgcatg
 241 caaaataaat gatatgcatg ttatctagca caagttacga ccgatttcag aagcagacca
 301 gaatcttcaa gcaccatgct cactaaacat gaccgtgaac ttgttatcta gttgtttaaa
 361 aattgtataa aacacaaata aagtcagaaa ttaatgaaac ttgtccacat gtcatgatat
 421 catatataga ggttgtgata aaaatttgat aatgtttcgg taaagttgtg acgtactatg
 481 tgtagaaacc taagtgacct acacataaaa tcatagagtt tcaatgtagt tcactcgaca
 541 aagactttgt caagtgtccg ataaaaagta ctcgacaaag aagccgttgt cgatgtactg
 601 ttcgtcgaga tctctttgtc gagtgtcaca ctaggcaaag tctttacgga gtgtttttca
 661 ggctttgaca ctcggcaaag cgctcgattc cagtagtgac agtaatttgc atcaaaaata
 721 gctgagagat ttaggccccg tttcaatctc acgggataaa gtttagcttc ctgctaaact
 781 ttagctatat gaattgaagt gctaaagttt agtttcaatt accaccatta gctctcctgt
 841 ttagattaca aatggctaaa agtagctaaa aaatagctgc taaagtttat ctcgcgagat
 901 tgaaacaggg ccttaaaatg agtcaactaa tagaccaact aattattagc tattagtcgt
 961 tagcttcttt aatctaagct aaaaccaact aatagcttat ttgttgaatt acaattagct
1021 caacggaatt ctctgttttt ctaaaaaaaa actgcccctc tcttacagca aattgtccgc
1081 tgcccgtcgt ccagatacaa tgaacgtacc tagtaggaac tcttttacac gctcggtcgc
1141 tcgccgcgga tcggagtccc cggaacacga caccactgtg gaacacgaca agtctgctc
1201 agaggcggcc acaccctggc gtgcaccgag ccggagcccg gataagcacg gtaaggagag
1261 tacggcggga cgtggcgacc cgtgtgtctg ctgccacgca gccttcctcc acgtagccgc
1321 gcggccgcgc cacgtaccag ggcccggcgc tggtataaat gcgcgccacc tccgctttag
1381 ttctgcatac agccaaccca a
```

*GGATCCAACACACACCCGAGGATATCACAGTCGACACTACACC*

Figure 2

```
   1 cggtatgaat ttggaaacaa attcagtact tttaaaaaaa tttgttgtag ggagcaaata
  61 atacataaaa taatttatgc attattttat tttttatttg taataatatg cttgaaacga
 121 taattcagta tgcatgttgt gccagtgtac tacacgggcg gggggagggg attgagtggg
 181 ccagcgcggt gcgtagggta gatgggctga aattgataac tcaagtccga ctaggttctc
 241 tttttatttc ccttccttt ctatttcct ttctttta tttcatgctt tcaaactaaa
 301 ttcaaattcg agttttgaat ttcagcttct aaattgtaca ctaaaattat atgataaggt
 361 aacccctact attactttta atttttttat tctacccat attgtttact taggggagaa
 421 taattgactt aatcacattc ttcctaggtt tcaattctca atctttcaaa tccacatttt
 481 tagatttcta ttttgaattt aaataccagt ttggatttag agttcaattt caaaatacac
 541 aaccaaaata ccagcatgaa tgcaaatata ttttatgttt atgtatttac ttttctttta
 601 tactttgctc aaaatagtta ttttcatgta tgaaactcaa taagcaagga actcacgtta
 661 ttatataacc taataggaat aatttaggta acataattta tcatcctctt gatttaaaag
 721 agatatgcct ccagaataag acacatacta aaaataactc taatattgaa taactaaagt
 781 cgtacaaatc tctactatta ttcctataaa ataataaaga actagctaca acttctttaa
 841 ggcattattc agggtttaca gcttgagagg catgaaccca tcctgtatac tcctggactt
 901 ggaagacaaa atgtcaacca aagtgaaagg ttttcttatg gttgctgcta agagatagat
 961 tgaacactag atctctccta agacgtcagg gcatgcgttt agactcctac acatgcgaaa
1021 actgcatctt acagttggaa gaaactatat ctcaccactt cctgcggtgt aactttgccc
1081 aaagatgttg gctcactgtt ggaatcactc cgccccgaac tttggatcta acgcttgcag
1141 tgctacatat tagagcaaga ctaacaatgc cgtggagaat ggaaggtatt ataaccatgt
1201 catggtgcat atggaaatgt cgaaataact ggatattcga aaacataccg ccaacggtgg
1261 cggcctgcaa ggaaatgttc aagactgaaa tgaactacat ctgctaccaa gttaagctcg
1321 agacaggagc taaaagtaga aactggatac aacactttgt aacatagtga cactcccctt
1381 ttcctttctt ttaccttaga actatacata caatccacat tcaataaaaa tttgtaggta
1441 cgccatacac actaccggaa tccggctctt tgccgagtgt gaggcgcttt gtcgagtgct
1501 ttttgtccag cactcggcaa aaaagtcttt gccatgtgcc gcactcggca aagtcctgct
1561 ctcggtaacg accgcgttta ccgagagcag gactctcgac acagaaatac actcgacaaa
1621 gaaatctttg ccgagagcca aacactcggc gaacggcagc gctcggcaaa gggtcgtcag
1681 ccgccgtcta aagctgacgg tcgttatctt tgtcgagtgc ccctcgtcc gacactcagt
1741 agagcaagct tgccgagtgc catcctgga cactcgataa agtatatttt atttttttt
1801 attttgccaa ccaaactttt tgtggtatgt tcctacacta tgtagatcta catgtaccat
1861 tttggcacaa ttacaaaaat gtttttctata actattagat ttagttcgtt tatttgaatt
1921 tcttcggaaa attcacatat gaactgcaag tcactcgaaa catgaaaaac cgtgcatgca
1981 aaataaatga tatgcatgtt atctagcaca agttacgacc gaattcagaa gcagaccaga
2041 atcttcaagc accatgctca ctaaacatga ccgtgaactt gttatccagt tgtttaaaaa
2101 ttgtataaaa cacaaataaa gtcagaaatt aatgaaactt gtccacatgt catgatatca
2161 tatatagagg ttgtgataaa aatttgataa tgtttcggta aagttgtgac gtactatgtg
2221 tagaaaccta agtgacctac acataaaatc atagagtttc aatgtagttc actcgacaaa
2281 gactttgtca agtgtccgat aaaagtatt cagcaaagaa gccgttgtcg atttactgtt
2341 cgtcgagatc tctttgccga gtgtcacact aggcaaagtc tttacggagt gttttcagg
2401 ctttgacact cggcaaagcg ctcgattcca gtagtgacag taatttgcat caaaaatagc
2461 cgagagattt aaaatgagtc aactaataga ccaactaatt attagctatt agtcgttagc
2521 ttctttaatc taagctaaaa ccaactaata gcttatttgt tgaattacaa ttagctcaac
2581 ggaattctct gttttttcta taaaaaaaag ggaaactgcc cctcatttac agcaaactgt
2641 ccgctgcctg tcgtccagat acaatgaacg tacctagtag gaactctttt acacgctcgg
2701 tcgctcgccg cggatcggag tcccaggaac acgacaccac tgtggaacac gacaaagtct
2761 gctcagaggc ggccacaccc tggcgtgcac cgagccggag ccggataag cacggtaagg
2821 agagtacggc gggacgtggc gacccgtgtg tctgctgcca cgcagccttc ctccacgtag
2881 ccgcgcggcc gcgccacgta ccagggcccg gcgctggtat aaatgcgcgc cacctccgct
2941 ttagttctgc atacagccaa cccaacacac acccgagcat atcacagtga cagacactac
3001 acgATG
```

Figure 5

METHODS TO INCREASE ANTIGENICITY OF MEMBRANE-BOUND POLYPEPTIDES PRODUCED IN PLANTS

REFERENCE TO RELATED APPLICATION

This application is a continuation-in-part of previously filed and application U.S. Ser. No. 13/558,874 filed Jul. 26, 2012, now abandoned, which claims priority to previously filed application U.S. Ser. No. 61/512,351, filed Jul. 27, 2011, the contents of each of which are incorporated herein by reference in their entirety.

This invention was made with government support under Grant Number 2R44AI068239-03A1 and 1 R43 AI068239-01A1 awarded by the National Institute of Health. The government has certain rights in the invention.

SEQUENCE LISTING

The instant application contains a Sequence Listing which has been submitted in ASCII format via EFS-Web in the parent application U.S. Ser. No. 13/558,874, and is hereby incorporated by reference in its entirety. Said ASCII copy, created on Jul. 26, 2012, is named AB00015.txt and is 19,187 bytes in size.

BACKGROUND OF THE INVENTION

Over the past decade, transgenic plants have been successfully used to express a variety of useful proteins. For example, production of proteases in plants has been achieved (See U.S. Pat. No. 6,087,558); along with production of aprotinin in plants (U.S. Pat. No. 5,824,870); and avidin (U.S. Pat. No. 5,767,379). A variety of mammalian bacterial and viral pathogen antigens are included in those proteins that have been successfully produced in plants, such as viral vaccines (U.S. Pat. No. 6,136,320), transmissible gastroenteritis and hepatitis vaccines (U.S. Pat. Nos. 5,914,123 and 6,034,298). These patents, as well as all references cited herein are incorporated herein by reference.

Many of the resulting peptides induced an immunogenic response in mice (Mason et al. (1998) *Vaccine* 16:13361343; Wigdorovitz et al. (1999) *Virology* 155:347-353), and humans (Kapusta et al. (1999) *FASEB J.* 13:1796-1799). After oral delivery, these vaccine candidates were immunogenic and could induce protection. Mice fed a basic diet plus corn expressing recombinant *Escherichia coli* heat-labile enterotoxin B-subunit (LtB) mounted a dose dependent IgG and IgA response (Streatfield et al. (2001) "Plant based vaccines—unique advances" *Vaccine* 19:2742-2748.) Some of the first edible vaccine technologies developed include transgenic potatoes expressing hepatitis B, TGEV and Norwalk virus antigens as well as various other viral antigens. (See, e.g., Thanavala et al. (1995) *Proc. Natl. Acad. Sci. U.S.A.* 92:3358-3361; U.S. Pat. No. 6,136,320; U.S. Pat. No. 6,034,298; U.S. Pat. No. 5,914,123; U.S. Pat. No. 5,612,487 and U.S. Pat. No. 5,484,719; Mason et al., (1996) *Proc. Natl. Acad. Sci.* 93:5335-5340; "VP1 protein for foot-and-mouth disease" (Wigdorovitz et al (1999) *Virology* 255:347-353)).

The utilization of transgenic plants for vaccine production has several potential benefits over traditional vaccine production methods. First, transgenic plants are usually constructed to express only a small antigenic portion of the pathogen or toxin, eliminating the possibility of infection or innate toxicity of the whole organism and reducing the potential for adverse reactions. Second, since there are no known human or animal pathogens that are able to infect plants, concerns with viral or prion contamination is eliminated. Third, immunogen production in transgenic crops relies on the same established technologies to sow, harvest, store, transport, and process the plant as those commonly used for food crops, making transgenic plants a very economical means of large-scale vaccine production. Fourth, expression of immunogens in the natural protein-storage compartments of plants maximizes stability, minimizes the need for refrigeration and keeps transportation and storage costs low. Fifth, formulation of multicomponent vaccines is possible by blending the seed of multiple transgenic plant lines into a single vaccine. Sixth, direct oral administration is possible when immunogens are expressed in commonly consumed food plants, such as grain, leading to the production of edible vaccines.

To be effective as a vaccine, the protein needs to be produced by the plant in a form that can elicit a protective response to a disease agent. This can be particularly challenging when the protein is a membrane-bound protein.

SUMMARY

Membrane-bound polypeptides are expressed in a plant composition where antigenicity and activity of the polypeptide is increased. When extracting a compound from the plant composition the process provides at least some phospholipids are associated with the membrane-bound polypeptide. The membrane-bound polypeptide produced by the process has increased antigenicity and is capable of producing an increased antigenic response in an animal when administered to the animal, or increased binding to a specific antibody. Such antigenicity is increased by increasing the amount of phospholipids that remain in the plant composition when extracting another compound or increasing the amount of phospholipids extracted with the membrane-bound polypeptide when extracting the membrane-bound polypeptide. In an embodiment when reducing the lipid content of the plant composition which comprises the polypeptide, the process provides for an increased amount of phospholipids remaining in the plant. In a further embodiment supercritical fluid extraction is used. With such increased antigenic response an animal may be protected from a disease agent when the membrane-bound polypeptide or plant, plant part or plant tissue is administered to the animal. Further, increased presence of phospholipids allows the membrane-bound protein to maintain a preferred structure such as a dimer versus monomer formation and the preferred formation provides for increased activity. Stability of the membrane-bound protein is also enhanced when fat content of plant compositions producing membrane-bound protein is reduced. In an embodiment the plant part may be seed, and in another embodiment may be germ of said seed.

DESCRIPTION OF DRAWINGS

FIG. 1 shows the sequence of the optimized hepatitis B surface antigen nucleotide sequence used in the experiments along with the Barley Alpha Amylase Signal Sequence (BAASS) in italics and the ATG start codon and stop codon sites in bold (entire sequence is SEQ ID NO: 1, the hepB sequences is SEQ ID NO: 2 and the BAASS sequence is SEQ ID NO: 3).

FIG. 2 shows the sequence of the Belanger et al. 1401 bp globulin-1 nucleotide sequence regulatory region (SEQ ID NO: 4) which was used in the experiments below and was followed by 43 extra bases (SEQ ID NO: 11, shown in italics just below the regulatory region sequence). The promoter is bases 1-1386 (SEQ ID NO: 5), the TATA box is at 1354-1360 and the 5'UTR is 1387-1401 (SEQ ID NO: 6).

FIG. 5 is the sequence of the extended globulin-1 promoter of U.S. Pat. No. 7,169,967. The entire sequence is SEQ ID NO: 7, with the promoter in regular font (SEQ ID NO: 8), the leader in bold (SEQ ID NO: 9) and the start site codon capitalized.

DETAILED DESCRIPTION

Figure 3:
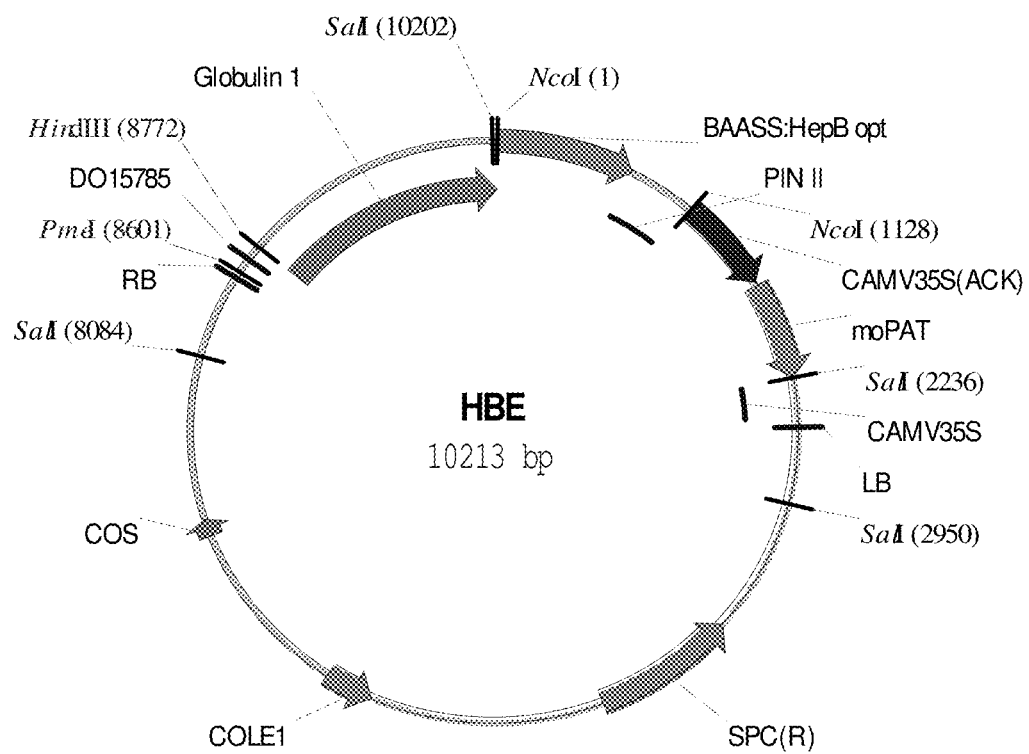
FIG. 3 is a map of the HBE construct.
Figure 4:
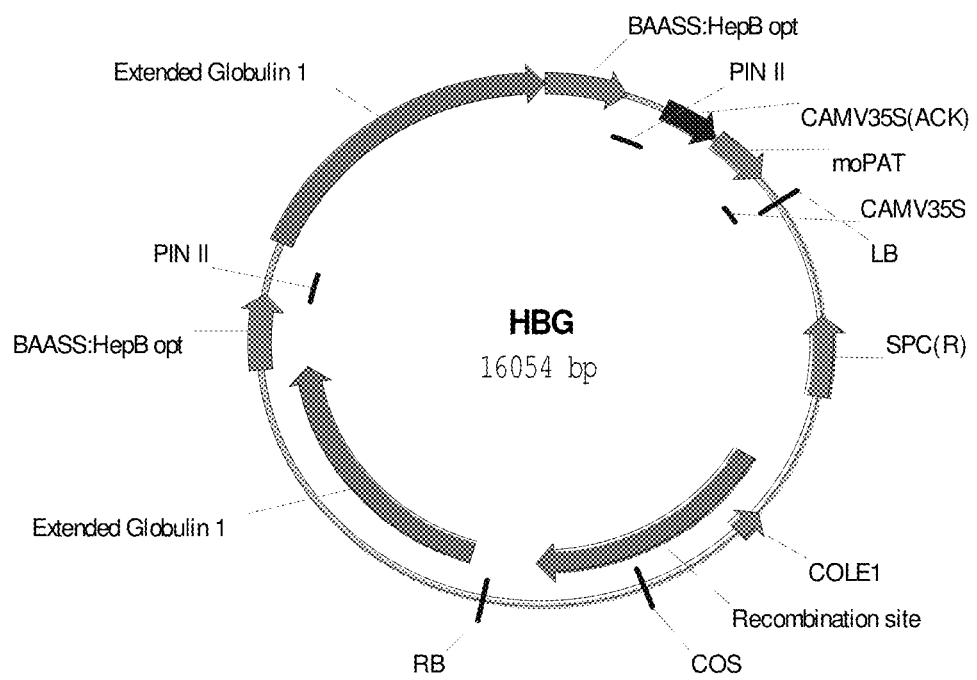
FIG. 4 is a map of the HBG construct.
Figure 6:
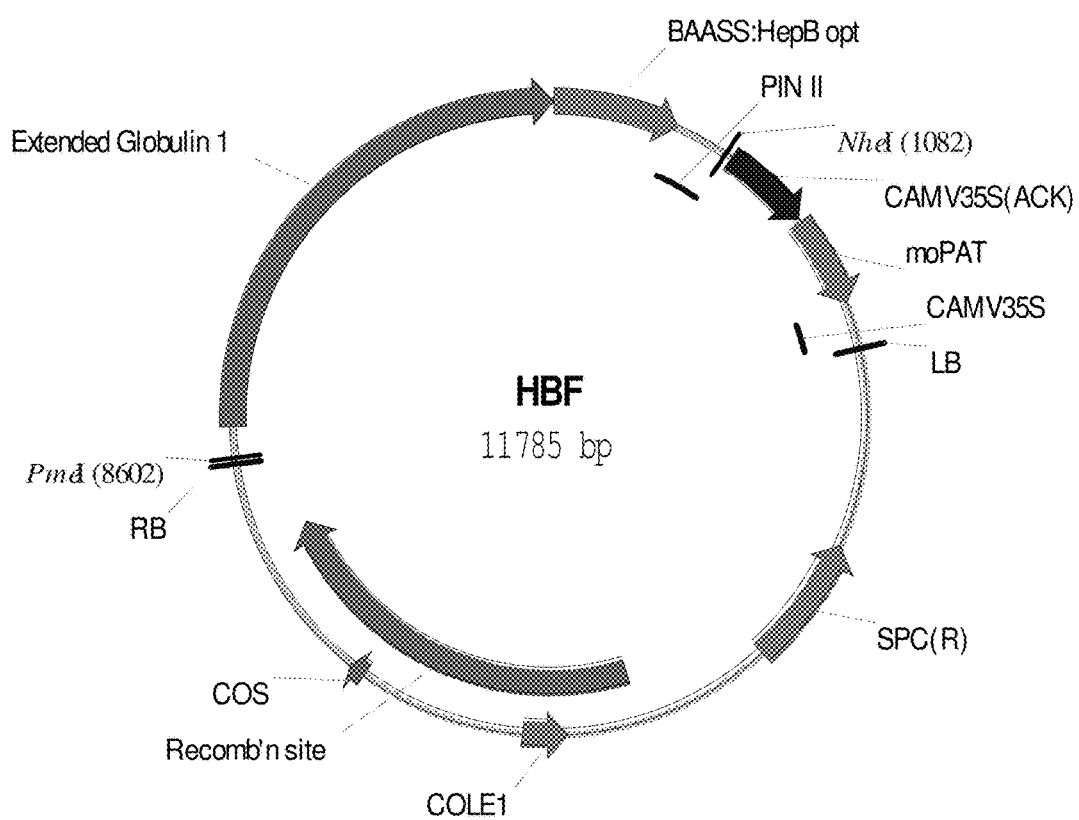
FIG. 6 is a map of the HBF construct.

A plant-produced polypeptide to be antigenic and to retain activity must be folded properly and produced in a form to retain activity and such that it is capable of being recognized by a specific antibody and/or elicit an animal's protective immune system so that a protective response is generated in the presence of the disease agent. If the animal's body does not recognize the polypeptide as an antigen, no immune reaction will occur and the polypeptide will not be effective in protecting the animal. This is particularly challenging when the polypeptide produced is a membrane-bound protein. Membrane proteins are more difficult to express in transgenic systems than soluble protein. Streatfield et al., (2003) *International Journal for Parasitology* 33 479-493. Scientists have noted that recombinant expression of integral membrane proteins is considered a major challenge. Eshaghi et al., "An efficient strategy for high-throughput expression screening of recombinant integral membrane proteins" *Protein Science,* 14:676-683 (2005). Proper processing and folding are among the many steps such proteins require for recognition by a specific antibody and/or producing a protective immune response.

The inventors have discovered it is possible to increase the antigenic nature of the polypeptide, in exposing the site of antigenicity of the membrane-bound polypeptide such that it is recognized as an antigen by the animal and an antigenic/protective response is generated. While it has been widely recognized that adding oil as an adjuvant to a vaccine will increase immune response, (See, e.g., Aucouturier et al. (2006) *Vaccine* Vol. 24, Supp. 2 pp.S44-S45 (International Workshop on Vaccine Adjuvants and Glycoconjugates, Varadero, Cuba Apr. 11-15 2004), the inventors have discovered that it is possible to improve exposure of the antigenic sites by reducing fat content of the plant material producing the polypeptide. Surprisingly, the removal of oil from the plant material producing the polypeptide improved recognition of the antigenic sites. Stability is also improved when the plant material expressing the membrane-bound peptide has reduced oil content. As illustrated in the table below, when grain was exposed to conditions of 55° C. for one year, the percent of hepatitis B protein survival in the grain was dramatically increased with supercritical fluid extraction (SFE)-defatted grain versus full fat grain.

TABLE 1

Stability of HBsAg in maize meal

| Treatment | % HBsAg survival in grain | |
|---|---|---|
| | Full Fat | SFE-defatted |
| 55° C. 1 year | 18 | 99 |

Grain was ground and stored at various temperatures or defatted prior to storage by SFE. Maize meal was extracted in buffer, HBsAg measured by ELISA and compared to the amount of HBsAg at time 0.

In one embodiment, by using a particular method of removal of oil content from the plant material, in which the phospholipids are preferentially left in the plant material, that is, where less phospholipids are removed in the extraction process compared to other lipids, antigenicity of the membrane-bound polypeptide is increased. In an embodiment supercritical fluid extraction (SFE) may be used.

Furthermore, when extracting the membrane-bound polypeptide from a the cell, antigenicity is increased upon administration of the polypeptide to an animal, when the extraction process includes an increased amount of phospholipids with the extracted membrane-bound polypeptide.

The inventors' research supports their theory that improved antigenicity is provided when at least some phospholipids are retained in association with the membrane-bound polypeptide. In referring to phospholipids being associated with the membrane-bound polypeptide is meant that increased amounts of phospholipids are retained in the plant composition where another compound is being extracted; or, when the membrane-bound polypeptide is being extracted, increased amounts of phospholipids are extracted with the membrane-bound polypeptide. An embodiment provides that when phospholipids are associated with the membrane-bound polypeptide, the polypeptide will, when administered to an animal, have an increased antigenic response compared to the process where a lower amount of phospholipids are associated with the polypeptide. In another embodiment binding of an antibody capable of binding to the membrane-bound polypeptide is increased compared to a plant-produced membrane-bound polypeptide in which a lower amount of phospholipids are associated with the polypeptide.

Thus when extracting a compound from the plant composition while retaining at least some membrane-bound polypeptide in the plant composition, at least some phospholipids remain in the plant composition. The compound being extracted may be any desired material within the plant composition where at least some membrane-bound polypeptide is retained in the plant composition and such a compound may be a composition or aggregate of molecules or a single molecule, and will vary depending upon the specific application. The compound could be an extract of the plant material (such as lipids, stilbenes, phenols, sugars, amino acids, proteins and the like) or a compound introduced into the plant. By way of example without limitation, such compounds can include diosgenin, sarsasapogenin or cholestorol, lipids including fatty acids such as C-8 to C-24 fatty acids, including octanoic acid, hexadecanoic acid, tetradecanoic acid and the like. As noted above, a wide variety of compounds can be introduced into the plant composition and extracted. Where the phospholipids remain in the plant composition to a greater degree, the membrane-bound polypeptide in the plant composition following the process has an increased antigenicity. Such a membrane-bound polypeptide will have an increased antigenic response when administered to an animal, and will bind to an antibody capable of binding to the polypeptide to a greater degree than a membrane-bound polypeptide produced in a plant where the process removes a higher degree of phospholipids.

In another embodiment, when extracting the membrane-bound polypeptide, the process employs compounds and methods that provide for including at least some phospholipids with the extracted membrane-bound polypeptide. The membrane-bound polypeptide following the process has an increased antigenicity. In an embodiment, when comparing antigenic response of an animal administered such a polypeptide to antigenic response of an animal administered a membrane-bound polypeptide obtained from plant material in which phospholipids are associated with the membrane-bound polypeptide in a lesser amount, the antigenic response is increased. In another embodiment, when comparing binding of an antibody capable of binding to the membrane-bound polypeptide, increased binding occurs compare to binding of the same antibody where the membrane-bound polypeptide is obtained from plant material in which phospholipids are associated with the membrane-bound polypeptide in a lower amount.

A person skilled in the art will be familiar with many different variations on compositions, compounds and methods that may be used that allow for phospholipids to be left in the host cell when extracting other compounds (such as oil) or which will allow for increased extraction of phospholipids along with the membrane-bound polypeptide. Hexane extraction, for example, removes most fat molecules including phospholipids. Extraction processes, however, such as SFE do not remove all the phospholipids. When extraction results in at least two fold, three-fold, four-fold, five-fold, six-fold, seven-fold, eight-fold, nine-fold, ten-fold, up to 100-fold or more or amounts in-between less phospholipids extracted when removing a compound from the plant composition. A likewise fold increase in extraction of phospholipids along with the membrane-bound polypeptide when extracting the membrane-bound polypeptide, provides for the improvements described. In one example, SFE is capable of extracting up to 10 to 100-fold (or more) fewer phospholipids than hexane treatment. See, List et al. (1989) "Oxidative Stability of Seed Oils Extracted with Supercritical Carbon Dioxide" *JAOCS, Vol.* 66, No. 1 pp. 98-101; Froning et al. (1990) "Extraction of Cholesterol and Other Lipids from Dried Egg Yolk Using Supercritical Carbon Dioxide" *Journal of Food Science Vol.* 55, No. 1, pp 95-98; Christianson et al. (1984) "Supercritical Fluid Extraction of Dry-Milled Corn Germ with Carbon Dioxide" *Journal of Food Science Vol.* 49 pp. 229-232; and Frederick and List (1982) "Characterization of Soybean Oil Extracted by Supercritical Carbon Dioxide and Hexane" *J. Agric. Food Chem.* 30, pp. 192-193. For example, a ten-fold less extraction of phospholipids was observed by Fredrick and List when removal of soybean flakes oil using a hot hexane extraction using a Soxhlet extractor for five hours was compared to extraction with the same flakes subjected to SFE $CO_2$ extraction at 5000 psi and 50° C. with flow rate at about 2 kg/hour over 11 hours. See Frederick and List (1982). Here, where providing for a hexane extraction in which 5 mL of hexane was used for every gram of ground maize material, mixing for 15 minutes at room temperature and filtered, the hexane-extracted maize material had lower immunogenicity than that subjected to SFE.

Thus, solvent extraction processes that provide for increased retention of phospholipids in the remaining material after other components are extracted or which provide for more phospholipids to be extracted with the polypeptide allow protection of the membrane-bound protein by those phospholipids. Phospholipids (which includes phosphatidylcholine, phosphatidylethanolamine, phosphatidylserine, phosphatidylinositols and phosphatidic acids) are important in cell membrane structure, including that of plants, microbes and animals. The lipids have two fatty acids, a glycerol unit, and a phosphate group. The phospholipid has a polar head (phosphate group) and non-polar tail (fatty acid chains). When extracting compounds from the host other than the polypeptide, such as oil, one employs a process that increases the phospholipids left in the host cell. In an embodiment such solvent extraction processes are those, such as SFE, that extract at least two fold, up to 10 fold fewer phospholipids, or extract even less, when removing oil or other hydrophobic compounds, as compared to a process using hexane for extraction. When extracting the polypeptide, the opposite result is desired, that is, extracting more phospholipids with the polypeptide.

By way of example, without limitation, an extensive discussion of processes that increase or decrease phospholipid extraction is found at U.S. Pat. No. 7,566,570 and WO2005072477, incorporated herein by reference in its entirety. Processes that increase extraction of nonpolar/neutral lipidic compounds or oils include aqueous soluble solvents including ethanol, methanol, and isopropanol; processes that increase extraction of polar lipidic compounds such as phospholipids include nonpolar organic solvents including hexane, chloroform, or heptane. Use of aliphatic alcohol at a higher than room temperature increases phospholipid extraction. SFE with carbon dioxide removes oil, but leaves phospholipids behind. Moreau et al. further describes various processes, such as accelerated solvent extraction, microwave-assisted extraction, solid fluid vortex extraction, Soxhlet and Soxtherm extraction and compared various components extracted with each process and variables that allow for fine tuning of what component is left or extracted from the host. See Moreau et al, (2003) "Pressurized liquid extraction of polar and nonpolar lipids in corn and oats with hexane, methylene chloride, isopropanol and ethanol" *JAOCS, Vol.* 80, No. 11 pp. 1063-1066; see also Matthäus et al. (2003) "Pressurized liquid extraction of polar and nonpolar lipids in corn and oats with hexane, methylene chloride, isopropanol, and ethanol: *JAOCS*, Vol. 80, No. 11 pp. 1063-1067. For example, without intending to be limiting, they note that more lipid was extracted as solvent polarity was increased, and for each individual solvent, more lipid was extracted at a higher (100° C.) versus lower (40° C.) temperature. Hexane extracts nearly all oil, including phospholipids. Still another example of extracting oils from a microbial biomass while leaving phospholipids behind is found at US patent application 20110263709 (incorporated herein by reference) and where options include use of a liquid or supercritical $CO_2$, tetrafluoromethane, ethane, ethylene, propane, propylene, butane, isobutane, isobutene, pentane, hexane, cyclohexane, benzene, toluene, xylenes, and mixtures thereof. Clearly, many such variations are available to one skilled in the art and any convenient method of controlling phospholipid extraction or retention in the host cell may be used.

The inventors have also found that where the extraction process provides that the membrane-bound polypeptide has a preferential molecule formation after the extraction process (which could be for example, a preferred formation of dimer as opposed to a monomer formation, or a preferred monomer or preferred trimer formation, depending on the polypeptide) the membrane-bound polypeptide will have an increased activity and antigenicity as compared to a process which does not provide for such preferential formation. By a preferred or preferential formation is meant that the process results in more polypeptide in the molecule formation favoring membrane activity. This higher amount of membrane-bound polypeptide in a formation that is preferred when the polypeptide is membrane-bound allows the polypeptide to retain activity. By way of further example, in the case of hepatitis B surface antigen, where a polypeptide has a preferred dimer formation as a membrane-bound polypeptide, the process results in a higher dimer formation of polypeptide as opposed to monomer formation.

The membrane-bound proteins which are useful include any polypeptide that is directed to a membrane-bound organelle and/or the cell membrane, and is not immediately secreted from the cell but remains associated with the membrane for a time. Therefore, membrane-bound proteins are inclusive of external membrane proteins (which are entirely outside of the cell membrane but bound to it by weak molecular attractions, such as ionic, hydrogen, and/or Van der Waals forces) and intrinsic membrane proteins that are embedded in the membrane. Membrane-bound proteins include, for example, integral membrane proteins, transmembrane proteins (which are amphipathic, having hydrophobic and hydrophilic regions and, therefore, having one or more membrane-spanning domains, such as type I and type II transmembrane proteins and multipass transmembrane receptors), peripheral membrane proteins, and lipid-anchored proteins. This includes many viral and glycoproteins. See, e.g., Grisshammer (2006) *Current Opinion in Biotechnology* 17:337-340 and http://blanco.biomol.uci.edu/mp-struc/listAll/list.

When referring to increasing the antigenicity of a polypeptide of a membrane-bound protein is meant that the polypeptide has increased recognition as an antigen when the plant cell is subject to an extraction process where an increased amount of phospholipids are extracted with the polypeptide, or remain in the cell with the polypeptide, compared to the polypeptide produced in plant material in which phospholipids are retained or associated with the polypeptide at a lower amount or not at all as a result of the extraction process. The same increased antigenicity and/or increased activity is provided when the process results in the membrane-bound polypeptide having a preferential molecule formation for the membrane-bound protein, whether monomer, dimer, trimer, or the like. The activity of the membrane-bound polypeptide may be measured in any of the myriad of ways suitable to determine if the desired formation is greater than the undesired formation, and/or to test if the desired activity of the membrane-bound polypeptide is retained to a higher degree than when produced by a method that associates phospholipids with the membrane-bound polypeptide to a lower degree. The desired activity measured, for example, may be triggering an increased immunogenic protective response when administered to an animal, increased binding with an antibody or other agent, or the like. Increased antigenicity or activity in one example provides a polypeptide can be recognized as an antigen by an antibody which binds to or responds to the specific polypeptide/antigen. The antibody will bind or respond to the antigen to a higher degree with the polypeptide so produced compared to a polypeptide associated to a lesser degree with phospholipids. In another example, the polypeptide is capable of producing an increased antigenic response when administered to an animal, compared to a polypeptide not subject to the process. As used here, an antigenic response refers to a protective immune response and the animal may or may not produce antibodies. The animal is protected from disease, as described further below. In another example, antibodies may be produced, and in one example B cells and T cells in animals can recognize a protein as an antigen.

One means of testing in vitro activity or whether the antigenic sites of a polypeptide are exposed is with the Enzyme-linked immunosorbent assay (ELISA). The ELISA has been known since 1971 and detects the presence of an antibody or antigen in a sample. In general, antigens solubilized in a buffer are coated on a surface. When an antibody specific to a polypeptide of the membrane-bound protein is applied over the surface it will bind the antigens. The presence or absence of these antibodies can be demonstrated when the antibody is conjugated to a marker enzyme. Adding the appropriate substrate will detect the amount of bound conjugate which can be quantified. The ELISA test takes many forms. In a typical assay, the antibody is linked with an enzyme and a substance added to convert the enzyme to a detectable signal, usually a color change in the substrate. A common ELISA assay is one which uses biotinylated anti-(protein) polyclonal antibodies and an alkaline phosphatase conjugate. For example, an ELISA used for quantitative determination of levels of a membrane-bound polypeptide can be an antibody sandwich assay, which utilizes polyclonal antibodies obtained commercially. The antibody is conjugated to alkaline phosphatases for detection. In another example, an ELISA assay to detect trypsin or trypsinogen uses biotinylated anti-trypsin or anti-trypsinogen polyclonal antibodies and a streptavidin-alkaline phosphatase conjugate. Obviously there are many variations available to the person skilled in the art, and the detection agent can include fluorogenic, electrochemiluminescent and real time PCR reporters. The specifics of the assay are not critical to the invention, as long as the polypeptide's ability to bind with a specific antibody is assayed. The assay may be qualitative or quantitative.

Another means of testing whether the polypeptide produced is active or antigenic and degree of antigenicity is to administer the polypeptide to an animal and determine whether an antibody is produced by the animal in response. A further means of testing whether the polypeptide is antigenic and degree of antigenicity is to administer the polypeptide to the animal and determine if a protective immune response is elicited when exposed to the disease-causing agent. The animal may be exposed to the disease causing agent before or after administration of the polypeptide. Measurement and determination of efficacy of any of the compositions and vaccines may be accomplished by any of the many methods available to one skilled in the art. By way of example, one may measure antibody production in the animal or measure disease morbidity or mortality. A few examples, without intending to be limiting, of diseases caused by membrane-bound polypeptides include hepatitis B, human and simian immunodeficiency virus, rabies virus (RABV), Norwalk virus, and Respiratory syncytial virus.

The activity of any membrane-bound polypeptide may be measured in a myriad of other ways. It will be depending upon the activity of the polypeptide, whether enzymatic, regulatory (such as receptor proteins) or the like. One can measure, by further example, transformation of a radioactive labeled substrate having a property to a second property as impacted by the polypeptide; ability to bind DNA or RNA; or depletion of components necessary for increased activity. For example, where the membrane-bound polypeptide is an enzyme, one can measure its enzymatic activity (see, e.g., Huber et al, (2009) "Measurement of membrane-bound human heme oxygenase-1 activity using a chemically defined assay system" *Drug Metabolism & Disposition*, vol. 37, no. 4 857-864); or where a receptor, measure with radiolabelled ligands (see. e.g., Davenport and Russell "Radioligand Binding assays: Theory and Practice" in *Current Directions in Radiopharmaceutical Research and Development* 169-179, S. J. Mather (ed.) 1996 Kluwer Academic Publishers; or measure cell proliferation or death as impacted by the polypeptide activity (see, e.g., various assays available from LIFE TECHNOLOGIES™ at lifetechnologies.com/us/en/home/references/molecular-probes-the-handbook/assays-for-cell-viability-proliferation-and-function/assays-for-cell-enumeration-cell-proliferation-and-cell-cycle.html). Clearly many methods are available and will become available to one skilled in the art in determining polypeptide activity.

The terms "protecting", "protection", "protective immunity" or "protective immune response," as used herein, are intended to mean that the animal mounts an active immune response to the vaccine or polypeptides of the present invention, such that upon exposure to the disease challenge, the animal is able to combat the infection. The animal may or may not produce antibodies in response, but the animal will have decreased morbidity or mortality resulting from administration of the vaccine. Thus, a protective immune response will decrease the incidence of morbidity and mortality from exposure to the microorganism among an animal. The animal will be protected from exposure to the disease-causing agent. In an embodiment, the animal may be protected by treating the animal which has already been exposed to the disease-causing agent by administration of the vaccine or polypeptide after such exposure. In such an instance there is also shown to be a lessening of morbidity and mortality. When referring to a disease-causing agent it meant the pathogen and is meant to include any such organism causing disease, for example, a virus, bacteria, fungus, or protozoan parasite. Those skilled in the art will understand that in a commercial animal setting, the production of a protective immune response may be assessed by evaluating the effects of vaccination on a group, flock or herd as a whole, e.g., there may still be morbidity and mortality in a minority of vaccinated animals. Furthermore, protection also includes a lessening in severity of any gross or histopathological changes and/or of symptoms of the disease, as compared to those changes or symptoms typically caused by the isolate in similar animals which are unprotected (i.e., relative to an appropriate control). Thus, a protective immune response will decrease the symptoms of the disease, which will vary according to the disease. Disease morbidity and/or mortality are reduced and where there also may be a reduced titer of infection upon exposure to the microorganism.

When referring to an improved protective response, antigenic response, and/or antigenicity can be, by way of example, a response that is of 25%, 50%, 75%, 100%, 200% or more or any amount in-between higher compared to antigenicity or response in which the plant composition is subjected to an extraction process with fewer phospholipids associated with the membrane-bound polypeptide. In another embodiment, stability can be in an example such a percentage lower where the plant material is not defatted. The processes described in an embodiment result in an increased mucosal and/or serum antibody response in an animal or both, and in a further embodiment, an increased fecal secretory IgA response. Increased mucosal antibody titers are observed with administration of a membrane-bound polypeptide produced by the processes described. Humoral response and serum titers may be increased.

As used herein, an antibody is defined in terms consistent with that recognized within the art: they are multi-subunit proteins produced by an organism in response to an antigen challenge. Antibodies include monoclonal antibodies and polyclonal antibodies, as well as fragments of such antibodies, including, but not limited to, Fab or F(ab')hd 2, and Fv fragments.

As used herein, an immunogenically effective amount is employed in a composition for administration to an animal and refers to an amount, which is effective in reducing, eliminating, treating, preventing or controlling the symptoms of the infections, diseases, disorders, or condition.

The invention can also produce a vaccine for administration to the animal. As used herein, the term "vaccine" as used herein refers to a pharmaceutical composition comprising at least one molecule, nucleic acid or polypeptide or fragment thereof that induces a protective response in an animal and possibly, but not necessarily, one or more additional components that enhance the activity of the active component. A vaccine may additionally comprise further components typical to pharmaceutical compositions. A vaccine may comprise one or simultaneously more than one of the elements described above.

The vaccine composition may be introduced into an animal, with a physiologically acceptable vehicle and/or adjuvant. Useful vehicles are well known in the art, and include, e.g., water, buffered water, saline, glycine, hyaluronic acid and the like. The resulting aqueous solutions may be packaged for use as is, or lyophilized, the lyophilized preparation being rehydrated prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. In an embodiment, the molecule is combined with a binder that assists in associating the molecule with feed, which is particularly useful for oral administration. Such a water resistant binding substance can be any substance having such properties. Examples include, without limitation, agarose or other sugar compounds, albumin, alginate or any similar composition.

In another embodiment, the membrane-bound polypeptide may be administered with other protective or desirable compounds which may be administered sequentially or progressively or alternately administered simultaneously in an admixture. Single or multiple administrations of the vaccine compositions can be carried out. Multiple administrations may be required to elicit sufficient levels of immunity.

In referring to administration of the membrane-bound polypeptide, the polypeptide may be "administered" in any suitable manner, including but not limited to, parenterally, by injection subcutaneously or intramuscularly, into an organ or cavity of the animal, reverse gavage (rectally), and oral, whether per os or ingestion of feed, immersion in a composition or substance containing the polypeptide, as well as transdermal or by gas exchange. The vaccine candidate can be administered by any means which includes, but is not limited to, syringes, nebulizers, misters, needleless injection devices, or microprojectile bombardment gene guns (Biolistic bombardment), via a liposome delivery system, naked delivery system, electroporation, viruses, vectors, viral vectors, or an ingestible delivery system wherein the protective molecules are consumed, for example, in feed or water or in any other suitable manner. Oral or immersion administration is a particular advantage in one embodiment. In another embodiment the extracted membrane-bound polypeptide or the plant material may be administered to the animal.

The quantity to be administered depends on the subject to be treated, including, for example, the capacity of the immune system of the individual to mount a protective response. Suitable regimes for initial administration and booster doses are also variable, but may include an initial administration followed by subsequent administrations. The need to provide an effective amount of the protective molecule will also need to be balanced with cost of providing higher amounts of the protective molecule. Put another way, using the process described here, the same dose or concentration of membrane-bound polypeptide has increased antigenicity and/or protective response and/or antibody production compared to a membrane-bound polypeptide also produced by the plant composition but where extraction does not employ the process described herein.

Oral boosting is provided in an embodiment, where the plant-produced membrane-bound polypeptide is orally administered to the animal following an initial administration or injection of a vaccine for the disease or comprising the membrane-bound polypeptide. By a booster administration is meant that the administration of the membrane-bound polypeptide follows at least one prior administration of the membrane-bound polypeptide but which may have been produced by the methods described here, or may be produced or isolated by a different process. Thus it may or may not have the same formation and may have some variation in the polypeptide. In the example provided herein, the hepatitis B surface antigen produced commercial and sol as RECOMBINEX® is administered to the animal, and followed by one or more booster doses of the hepatitis B surface antigen produced by the process here. An initial administration in an embodiment is injection of a vaccine for the disease or condition followed by oral administration of the plant produced membrane-bound polypeptide. A further embodiment provides an edible form of the plant composition is orally administered to the animal. The booster administration can be provided once, twice, three times or as many times as is desired, and is especially facilitated when the plant composition comprising the polypeptide is administered. The plant composition can be administered in its raw form, depending upon the plant material used, or can be further processed. The plant material, for example, could be provided as meal, ground seeds, flour, flakes, or the like. It can be mixed with other materials that aid in improving flavor, texture or the like. A wide variety of products can be prepared from a mix of plant flour and liquids to form a dough, and the wafers described herein as one example. It may be cooked or provided raw, and in various sizes, textures or shapes.

The polypeptide may be administered after extraction from the host, plant, or plant material comprising the polypeptide. The polypeptide may be extracted after the plant material fat content is reduced, and the plant material may be administered after fat content has been reduced.

When referring to fat is meant the lipid or oil content of the plant material. Defatting processes take many forms, including mechanical, using presses or expellers, for example, or chemical compositions. Reduction of fat content of the plant material can be achieved using any of the many methods available to one skilled in the art. Organic solvents are commonly used to extract oil from plant material by treatment with a solvent which is often a lower carbon alkane, such as propane, butane or hexane. Oil has been traditionally removed from the plant material such as the germ using hexane solvent extraction processes. As discussed above, when increasing the antigenicity of the membrane-bound polypeptide, processes for fat reduction that increase the amount of phospholipids in the plant material compared to a hexane extraction process may be used. In an embodiment, the method of defatting plant material uses the high pressure process called supercritical fluid extraction (SFE). A supercritical fluid is used, any substance at a temperature and pressure above its critical point where distinct liquid and gas phases do not exist. The most common for food uses employs carbon dioxide. In brief, a typical process will move the fluid into a heating zone where it is heated to supercritical conditions and then diffused into a solid matrix and dissolves the material which is to be extracted. See, e.g., R. S. Mohamed and G. A. Mansoori, "Extraction Technology in Food Processing" *Food Technology Magazine June,* 2002, The World Markets Research Centre, London, UK; Brunner, G. (2005) "Supercritical fluids: technology and application to food processing" *Journal of Food Engineering,* 67, 21-33. In an embodiment, it is less desirable to use strong detergents at high levels (an example is Triton X-100 at 1%), in that it may interfere with assays and would reduce the likelihood the plant material could be used as feed in that it would not be suitable for feeding to an animal.

As will be evident to one skilled in the art, SFE has been known for over one hundred years and is not confined to any particular machine or variations of the process. See general discussions at, for example, Reid et al. *The Properties of Gases and Liquids* New York: McGraw-Hill (1987) ISBN 0070517991; *Taylor Supercritical Fluid Extraction (Techniques in Analytical Chemistry)* Wiley-Interscience (1996) ISBN-13: 978-0471119906. See also, for example, DeCrosta et al, U.S. Pat. No. 5,252,729 ("Extraction of compounds from plant materials using supercritical fluids"; Eldridge et al. U.S. Pat. No. 4,493,854 "Production of defatted soybean products by supercritical fluid extraction"; Sevenants et al., U.S. Pat. No. 4,675,198 "Removal of textured vegetable product off-flavor by supercritical fluid or liquid extraction"; Dietmar et al. U.S. Pat. No. 5,120,558 "Process for the supercritical extraction and fractionation of spices".

Oil content of the germ portion of a maize seed, for example, is typically 30% oil (Bunge Milling, http://bungenorthamerica.com/news/pubs/03_bunge_milling_process_diagram.pdf) In an embodiment, at least 50% of the fat of a plant seed or germ is removed in order to make the cost of defatting practical to use. An embodiment provides at least 80% of the fat is removed, in another at least 90% of fat removed, or amounts in between at least 50% and up. A further embodiment provides that at least 95% fat is removed or to the point that no fat is detected. In another embodiment, the fat is removed until the process no longer removes further fat. As discussed herein, in an embodiment, such as with the supercritical fluid extraction process of removing fat, at least some of the phospholipids are retained. In an embodiment at least two fold, up to 10 fold (or more) fewer phospholipids are removed when compared to the hexane extraction process. Thus in this instance when referring to the amount of fat removed when such a process as the SFE process is used is intended to retain the antigenicity enhancing properties of the process.

The term plant composition refers to plant or plant material or plant part or plant tissue or plant cell including collection of plant cells. It is used broadly herein to include any plant at any stage of development, or to part of a plant, including a plant cutting, a plant cell culture, a plant organ, a plant seed, and a plantlet. Plant seed parts, for example, include the pericarp or kernel, the embryo or germ, and the endoplasm. A plant cell is the structural and physiological unit of the plant, comprising a protoplast and a cell wall. A plant cell can be in the form of an isolated single cell or aggregate of cells such as a friable callus, or a cultured cell, or can be part of a higher organized unit, for example, a plant tissue, plant organ, or plant. Thus, a plant cell can be a protoplast, a gamete producing cell, or a cell or collection of cells that can regenerate into a whole plant. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like. In an embodiment, the tissue culture will preferably be capable of regenerating plants. Preferably, the regenerable cells in such tissue cultures will be embryos, protoplasts, meristematic cells, callus, pollen, leaves, anthers, roots, root tips, silk, flowers, kernels, ears, cobs, husks or stalks. Still further, plants may be regenerated from the tissue cultures.

When using the germ (embryo) of the plant, one can separate the germ from the remainder of the seed and use it as a source of the membrane-bound polypeptide. In one embodiment, the promoter driving the polypeptide may be one which is preferentially expressed in the seed, or preferentially expressed in the embryo of the plant, thus even further increasing available polypeptide. Such promoters are discussed below, and methods of using germ as the source of protein are discussed at U.S. Pat. Nos. 7,179,961 and 6,504,085 incorporated herein by reference in their entirety.

A "construct" is a package of genetic material inserted into the genome of a cell via various techniques. A "vector" is any means for the transfer of a nucleic acid into a host cell. A vector may be a replicon to which a DNA segment may be attached so as to bring about the replication of the attached segment. A "replicon" is any genetic element (e.g., plasmid, phage, cosmid, chromosome, virus) that functions as an autonomous unit of DNA or RNA replication in vivo, i.e., capable of replication under its own control. In addition to a nucleic acid, a vector may also contain one or more regulatory regions, and/or selectable markers useful in selecting, measuring, and monitoring nucleic acid transfer results (transfer to which tissues, duration of expression, etc.).

A "cassette" refers to a segment of DNA that can be inserted into a vector at specific restriction sites. The segment of DNA encodes a polypeptide of interest or produces RNA, and the cassette and restriction sites are designed to ensure insertion of the cassette in the proper reading frame for transcription and translation.

A cell has been "transfected" by exogenous or heterologous DNA or RNA when such DNA or RNA has been introduced inside the cell.

As used herein, the terms nucleic acid or polynucleotide refer to deoxyribonucleotides or ribonucleotides and polymers thereof in either single- or double-stranded form. As such, the terms include RNA and DNA, which can be a gene or a portion thereof, a cDNA, a synthetic polydeoxyribonucleic acid sequence, or the like, and can be single-stranded or double-stranded, as well as a DNA/RNA hybrid. Furthermore, the terms are used herein to include naturally-occurring nucleic acid molecules, which can be isolated from a cell, as well as synthetic molecules, which can be prepared, for example, by methods of chemical synthesis or by enzymatic methods such as by the polymerase chain reaction (PCR). Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260:2605-2608; Rossolini et al. (1994) *Mol. Cell. Probes* 8:91-98). The term nucleic acid is used interchangeably with gene, cDNA, and mRNA encoded by a gene.

As used herein, a nucleotide segment is referred to as operably linked when it is placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Operably linked elements may be contiguous or non-contiguous. When used to refer to the joining of two protein coding regions, by operably linked it is intended that the coding regions are in the same reading frame. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions.

Nucleic acids include those that encode an entire polypeptide or fragment thereof. The invention includes not only the exemplified nucleic acids that include the nucleotide sequences as set forth herein, but also nucleic acids that are substantially identical to, correspond to, or substantially complementary to, the exemplified embodiments. For example, the invention includes nucleic acids that include a nucleotide sequence that is at least about 70% identical to one that is set forth herein, more preferably at least 75%, still more preferably at least 80%, more preferably at least 85%, 86%, 87%, 88%, 89% still more preferably at least 90%, 91%, 92%, 93%, 94%, and even more preferably at least about 95%, 96%, 97%, 98%, 99%, 100% identical (or any percentage in between) to an exemplified nucleotide sequence. The nucleotide sequence may be modified as described previously, so long any antigenic polypeptide encoded is capable of inducing the generation of a protective response.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques. In some embodiments, the nucleotide sequences that encode a protective polypeptide are preferably optimized for expression in a particular host cell (e.g., yeast, mammalian, plant, fungal, and the like) used to produce the polypeptide or RNA.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" referred to herein as a "variant" where the alteration results in the substitution of an amino acid with a chemically similar amino acid. Conservative substitution tables providing functionally similar amino acids are well known in the art. See, for example, Davis et al., "Basic Methods in Molecular Biology" Appleton & Lange, Norwalk, Conn. (1994). Such conservatively modified variants are in addition to and do not exclude polymorphic variants, interspecies homologs, and alleles.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, 1984, Proteins).

The isolated variant proteins can be purified from cells that naturally express it, purified from cells that have been altered to express it (recombinant), or synthesized using known protein synthesis methods. For example, a nucleic acid molecule encoding the variant polypeptide is cloned into an expression vector, the expression vector introduced into a host cell and the variant protein expressed in the host cell. The variant protein can then be isolated from the cells by an appropriate purification scheme using standard protein purification techniques.

A protein is comprised of an amino acid sequence when the amino acid sequence is at least part of the final amino acid sequence of the protein. In such a fashion, the protein may be a the original polypeptide, a variant polypeptide and/or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids.

The variant proteins used in the present invention can be attached to heterologous sequences to form chimeric or fusion proteins. Such chimeric and fusion proteins comprise a variant protein fused in-frame to a heterologous protein having an amino acid sequence not substantially homologous to the variant protein. The heterologous protein can be fused to the N-terminus or C-terminus of the variant protein.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., eds. (1995) *Current Protocols in Molecular Biology* (Greene Publishing and Wiley-Interscience, New York). Moreover, many expression vectors are commercially available that already encode a fusion moiety (e.g., a GST protein). A variant protein-encoding nucleic acid can be cloned into such an expression vector such that the fusion moiety is linked in-frame to the variant protein.

Polypeptides sometimes contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art. Accordingly, the variant peptides of the present invention also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Fragments of the variant proteins may be used, in addition to proteins and peptides that comprise and consist of such fragments, provided that such fragments act as an antigen and/or provide treatment for and/or protection against infections as provided by the present invention.

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1.0 M NaCl, 1% SDS at 37° C., and a wash in 0.1×SSC at 60 to 65° C.

Specificity is also the function of post-hybridization washes, the critical factors being the ionic strength and temperature of the final wash solution. For DNA-DNA hybrids, the $T_m$ can be approximated from the equation $T_m=81.5°$ C.$+16.6$ (log M)$+0.41$(% GC)$-0.61$(% form.)$-500/L$, where M is the molarity of monovalent cations, % GC is the percentage of guanosine and cytosine nucleotides in the DNA, % form is the percentage of formamide in the hybridization solution, and L is the length of the hybrid in base pairs (Meinkoth and Wahl, 1984). The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted for sequences of the desired identity to hybridize. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11 to 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Ausubel et al., eds. (1995) *Current Protocols in Molecular Biology* (Greene Publishing and Wiley-Interscience, New York) and Sambrook et al., (1989) *Molecular Cloning: A Laboratory Manual,* 2nd Edition. Cold Spring Harbor Laboratory Press, Plainview, N.Y.

Thus, isolated sequences that have promoter activity and which hybridize under stringent conditions to promoter sequences, or to fragments thereof, are encompassed by the processes described.

The following terms are used to describe the sequence relationships between two or more nucleic acids or polynucleotides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length promoter sequence, or the complete promoter sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to accurately reflect the similarity to a reference sequence due to inclusion of gaps in the polynucleotide sequence a gap penalty is typically introduced and is subtracted from the number of matches. Methods of alignment of sequences for comparison are well known in the art. Thus, the determination of percent identity between any two sequences can be accomplished using a mathematical algorithm. Optimal alignment of sequences for comparison can use any means to analyze sequence identity (homology) known in the art, e.g., by the progressive alignment method of termed "PILEUP" (Morrison, Mol. Biol. Evol. 14:428-441 (1997), as an example of the use of PILEUP); by the local homology algorithm of Smith & Waterman (Adv. Appl. Math. 2: 482 (1981)); by the homology alignment algorithm of Needleman & Wunsch (J. Mol. Biol. 48:443 (1970)); by the search for similarity method of Pearson (Proc. Natl. Acad. Sci. USA 85: 2444 (1988)); by computerized implementations of these algorithms (e.g., GAP, BEST FIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by, e.g., Higgins, Gene 73: 237-244 (1988); Corpet, Nucleic Acids Res. 16:10881-10890 (1988); Huang, Computer Applications in the Biosciences 8:155-165 (1992); and Pearson, Methods in Mol. Biol. 24:307-331 (1994); Pfam (Sonnhammer, Nucleic Acids Res. 26:322-325 (1998); TreeAlign (Hein, Methods Mol. Biol. 25:349-364 (1994); MEG-ALIGN, and SAM sequence alignment computer programs; or, by manual visual inspection.

Another example of algorithm that is suitable for determining sequence similarity is the BLAST algorithm, which is described in Altschul et al, J. Mol. Biol. 215: 403-410 (1990). The BLAST programs (Basic Local Alignment Search Tool) of Altschul, S. F., et al., (1993) J. Mol. Biol. 215:403-410) searches under default parameters for identity to sequences contained in the BLAST "GENEMBL" database. A sequence can be analyzed for identity to all publicly available DNA sequences contained in the GENEMBL database using the BLASTN algorithm under the default parameters.

Software for performing BLAST analyses is publicly available through the National Center for Biotechnology Information, www.ncbi.nlm.nih.gov/; see also Zhang, Genome Res. 7:649-656 (1997) for the "PowerBLAST" variation. This algorithm involves first identifying high scoring sequence pairs (HSPs) by identifying short words of length W in the query sequence that either match or satisfy some positive valued threshold score T when aligned with a word of the same length in a database sequence. T is referred to as the neighborhood word score threshold (Altschul et al, J. Mol. Biol. 215: 403-410 (1990)). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a wordlength (W) of 11, the BLOSUM62 scoring matrix (see Henikoff, Proc. Natl. Acad. Sci. USA 89:10915-10919 (1992)) alignments (B) of 50, expectation (E) of 10, M=5, N=-4, and a comparison of both strands. The term BLAST refers to the BLAST algorithm which performs a statistical analysis of the similarity between two sequences; see, e.g., Karlin, Proc. Natl. Acad. Sci. USA 90:5873-5787 (1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. In an embodiment, GAP (Global Alignment Program) can be used. GAP uses the algorithm of Needleman and Wunsch J. Mol. Biol. 48:443-453 (1970) to find the alignment of two complete sequences that maximizes the number of matches and minimizes the number of gaps. Default gap creation penalty values and gap extension penalty values in the commonly used Version 10 of the Wisconsin Package® (Accelrys, Inc., San Diego, Calif.) for protein sequences are 8 and 2, respectively. For nucleotide sequences the default gap creation penalty is 50 while the default gap extension penalty is 3. Percent Similarity is the percent of the symbols that are similar. Symbols that are across from gaps are ignored. A similarity is scored when the scoring matrix value for a pair of symbols is greater than or equal to 0.50, the similarity threshold. A general purpose scoring system is the BLOSUM62 matrix (Henikoff and Henikoff, Proteins, 17: 49-61 (1993)), which is currently the default choice for BLAST programs. BLOSUM62 uses a combination of three matrices to cover all contingencies. Altschul, J. Mol. Biol. 36: 290-300 (1993), herein incorporated by reference in its entirety and is the scoring matrix used in Version 10 of the Wisconsin Package® (Accelrys, Inc., San Diego, Calif.) (see Henikoff & Henikoff (1989) Proc. Natl. Acad. Sci. USA 89:10915).

As used herein, "sequence identity" or "identity" in the context of two nucleic acid sequences makes reference to the residues in the two sequences that are the same when aligned for maximum correspondence over a specified comparison window.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

Identity to a sequence used herein would mean a polynucleotide sequence having at least 65% sequence identity, more preferably at least 70% sequence identity, more preferably at least 75% sequence identity, more preferably at least 80% identity, more preferably at least 85% 86%, 87%, 88%, 89%, 90%, 91%, 92%, 93%, 94%, 95%, 96%, 97%, 98%, 99% sequence identity.

The membrane-bound polypeptide-encoding nucleic acid molecule may be combined with any number of other components to be introduced into the plant, including combined with another gene of interest to be expressed in the host. The "gene of interest" refers to a nucleotide sequence that encodes for another desired polypeptide or protein but also may refer to nucleotide sequences that do not constitute an entire gene, and which do not necessarily encode a polypeptide or protein. For example, when used in a homologous recombination process, the nucleic acid molecule may be placed in a construct with a sequence that targets and area of the chromosome in the plant but may not encode a protein. The gene can be used to drive mRNA that can be used for a silencing system, such as antisense, and in that instance, no protein is produced. Means of increasing or inhibiting a protein are well known to one skilled in the art and, by way of example, may include, transgenic expression, antisense suppression, co-suppression methods including but not limited to: RNA interference, gene activation or suppression using transcription factors and/or repressors, mutagenesis including transposon tagging, directed and site-specific mutagenesis, chromosome engineering and, homologous recombination. In the case of use with homologous recombination, no in vivo construct will be required. If desired, the membrane-bound polypeptide-encoding nucleic acid molecule or gene of interest can be optimized for host or other plant translation by optimizing the codons used for host or plants and the sequence around the translational start site for host or plants. Sequences resulting in potential mRNA instability can also be avoided.

In general, the methods available for construction of recombinant genes, optionally comprising various modifications for improved expression, can differ in detail and any of the methods available to one skilled in the art may be used in the invention. However, conventionally employed methods include PCR amplification, or the designing and synthesis of overlapping, complementary synthetic oligonucleotides, which are annealed and ligated together to yield a gene with convenient restriction sites for cloning, or subcloning from another already cloned source, or cloning from a library. The methods involved are standard methods for a molecular biologist (Sambrook et al., (1989) *Molecular Cloning: A Laboratory Manual,* 2nd Edition. Cold Spring Harbor Laboratory Press, Plainview, N.Y.).

Once the gene is engineered to contain desired features, such as the desired subcellular localization sequences, it may then be placed into an expression vector by standard methods. The selection of an appropriate expression vector will depend upon the method of introducing the expression vector into host cells. A typical expression vector contains prokaryotic DNA elements coding for a bacterial origin of replication and an antibiotic resistance gene to provide for the growth and selection of the expression vector in the bacterial host; a cloning site for insertion of an exogenous DNA sequence; eukaryotic DNA elements that control initiation of transcription of the exogenous gene; and DNA elements that control the processing of transcripts, such as transcription termination/polyadenylation sequences. It also can contain such sequences as are needed for the eventual integration of the vector into the host chromosome.

By "promoter" is meant a regulatory region of DNA capable of regulating the transcription of a sequence linked thereto. It usually comprises a TATA box capable of directing RNA polymerase II to initiate RNA synthesis at the appropriate transcription initiation site for a particular coding sequence. The promoter is the minimal sequence sufficient to direct transcription in a desired manner. The term "regulatory region" is also used to refer to the sequence capable of initiating transcription in a desired manner.

The membrane-bound polypeptide—encoding nucleic acid molecule may be used in conjunction with its own or another promoter. In one embodiment, a selection marker and the membrane-bound polypeptide—encoding nucleic acid molecule or gene of interest can be functionally linked to the same promoter. In another embodiment, they can be functionally linked to different promoters. In yet third and fourth embodiments, the expression vector can contain two or more genes of interest that can be linked to the same promoter or different promoters. For example, one promoter can be used to drive the membrane-bound polypeptide—encoding nucleic acid molecule and gene of interest and the selectable marker, or a different promoter used for one or each. These other promoter elements can be those that are constitutive or sufficient to render promoter-dependent gene expression controllable as being cell-type specific, tissue-specific or time or developmental stage specific, or being inducible by external signals or agents. Such elements may be located in the 5' or 3' regions of the gene. Although the additional promoter may be the endogenous promoter of a structural gene of interest, the promoter can also be a foreign regulatory sequence. Promoter elements employed to control expression of product proteins and the selection gene can be any host-compatible promoters. These can be plant gene promoters, such as, for example, the ubiquitin promoter (European patent application no. 0 342 926); the promoter for the small subunit of ribulose-1,5-bis-phosphate carboxylase (ssRUBISCO) (Coruzzi et al., 1984; Broglie et al., 1984); or promoters from the tumor-inducing plasmids from *Agrobacterium tumefaciens*, such as the nopaline synthase, octopine synthase and mannopine synthase promoters (Velten and Schell, 1985) that have plant activity; or viral promoters such as the cauliflower mosaic virus (CaMV) 19S and 35S promoters (Guilley et al., 1982; Odell et al., 1985), the figwort mosaic virus FLt promoter (Maiti et al., 1997) or the coat protein promoter of TMV (Grdzelishvili et al., 2000). Alternatively, plant promoters such as heat shock promoters for example soybean hsp 17.5-E (Gurley et al., 1986); or ethanol-inducible promoters (Caddick et al., 1998) may be used. See International Patent Application No. WO 91/19806 for a review of illustrative plant promoters suitably employed.

A promoter can additionally comprise other recognition sequences generally positioned upstream or 5' to the TATA box, referred to as upstream promoter elements, which influence the transcription initiation rate. It is recognized that having identified the nucleotide sequences for a promoter region, it is within the state of the art to isolate and identify further regulatory elements in the 5' region upstream from the particular promoter region identified herein. Thus the promoter region is generally further defined by comprising upstream regulatory elements such as those responsible for tissue and temporal expression of the coding sequence, enhancers and the like.

Tissue-preferred promoters can be utilized to target enhanced transcription and/or expression within a particular tissue. When referring to preferential expression, what is meant is expression at a higher level in the particular tissue than in other tissue. Examples of these types of promoters include seed preferred expression such as that provided by the phaseolin promoter (Bustos et al. (1989) *The Plant Cell* Vol. 1, 839-853). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, an Ltp1 (See, for example, U.S. Pat. No. 7,550,579), an Ltp2 (Opsahl-Sorteberg, H-G. et al., (2004) *Gene* 341:49-58 and U.S. Pat. No. 5,525,716), and oleosin genes. See also WO 00/12733, where seed-preferred promoters from end1 and end2 genes are disclosed. Seed-preferred promoters also include those promoters that direct gene expression predominantly to specific tissues within the seed such as, for example, the endosperm-preferred promoter of γ-zein, the cryptic promoter from tobacco (Fobert et al. (1994) "T-DNA tagging of a seed coat-specific cryptic promoter in tobacco" *Plant J.* 4: 567-577), the P-gene promoter from corn (Chopra et al. (1996) "Alleles of the maize P gene with distinct tissue specificities encode Myb-homologous proteins with C-terminal replacements" *Plant Cell* 7:1149-1158, Erratum in *Plant Cell* 1997, 1:109), the globulin-1 promoter from corn (Belanger and Kriz (1991) "Molecular basis for Allelic Polymorphism of the maize Globulin-1 gene" *Genetics* 129: 863-972 and GenBank accession No. L22344), promoters that direct expression to the seed coat or hull of corn kernels, for example the pericarp-specific glutamine synthetase promoter (Muhitch et al., (2002) "Isolation of a Promoter Sequene From the Glutamine Synthetase$_{1\text{-}2}$ Gene Capable of Conferring Tissue-Specific Gene Expression in Transgenic Maize" *Plant Science* 163:865-872 and GenBank accession number AF359511) and to the embryo (germ) such as that disclosed at U.S. Pat. No. 7,169,967. When referring to an embryo preferred promoter is meant that it expresses an operably linked sequence to a higher degree in embryo tissue that in other plant tissue. It may express during embryo development, along with expression at other stages, may express strongly during embryo development and to a much lesser degree at other times.

The range of available promoters includes inducible promoters. An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the actin of a pathogen or disease agent such as a virus. A cell containing an inducible regulatory element may be exposed to an inducer by externally applying the inducer to the cell or plant such as by spraying, watering, heating or similar methods.

Any inducible promoter can be used. See Ward et al. Plant Mol. Biol. 22: 361-366 (1993). Exemplary inducible promoters include ecdysone receptor promoters, U.S. Pat. No. 6,504,082; promoters from the ACE1 system which responds to copper (Mett et al. PNAS 90: 4567-4571 (1993)); In2-1 and In2-2 gene from maize which respond to benzenesulfonamide herbicide safeners (U.S. Pat. No. 5,364,780; Hershey et al., Mol. Gen. Genetics 227: 229-237 (1991) and Gatz et al., *Mol. Gen. Genetics* 243: 32-38 (1994)) Tet repressor from Tn10 (Gatz et al., *Mol. Gen. Genet.* 227: 229-237 (1991); or from a steroid hormone gene, the transcriptional activity of which is induced by a glucocorticosteroid hormone. Schena et al., *Proc. Natl. Acad. Sci. U.S.A.* 88: 10421 (1991); the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156).

Other components of the vector may be included, also depending upon intended use of the gene. Examples include selectable markers, targeting or regulatory sequences, stabilizing or leader sequences, introns etc. General descriptions and examples of plant expression vectors and reporter genes can be found in Gruber, et al., "Vectors for Plant Transformation" in *Method in Plant Molecular Biology and Biotechnology*, Glick et al eds; CRC Press pp. 89-119 (1993). The selection of an appropriate expression vector will depend upon the host and the method of introducing the expression vector into the host. The expression cassette will also include at the 3' terminus of the heterologous nucleotide sequence of interest, a transcriptional and translational termination region functional in plants.

In one embodiment, the expression vector also contains a gene encoding a selectable or scoreable marker that is operably or functionally linked to a promoter that controls transcription initiation. Examples of selectable markers include those that confer resistance to antimetabolites such as herbicides or antibiotics, for example, dihydrofolate reductase, which confers resistance to methotrexate (Reiss, (1994) *Plant Physiol.* (Life Sci. Adv.) 13:143-149; see also Herrera Estrella et al., (1983) *Nature* 303:209-213; Meijer et al., (1991) *Plant Mol. Biol.* 16:807-820); neomycin phosphotransferase, which confers resistance to the aminoglycosides neomycin, kanamycin and paromycin (Herrera-Estrella, (1983) *EMBO J.* 2:987-995, and Fraley et al. (1983) *Proc. Natl. Acad. Sci. USA* 80:4803) and hygro, which confers resistance to hygromycin (Marsh, (1984) *Gene* 32:481-485; see also Waldron et al., (1985) *Plant Mol. Biol.* 5:103-108; Zhijian et al., (1995) *Plant Science* 108:219-227); trpB, which allows cells to utilize indole in place of tryptophan; hisD, which allows cells to utilize histinol in place of histidine (Hartman, (1988) *Proc. Natl. Acad. Sci., USA* 85:8047); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, (1987), in: *Current Communications in Molecular Biology*, Cold Spring Harbor Laboratory ed.); and deaminase from *Aspergillus terreus*, which confers resistance to Blasticidin S (Tamura, (1995) *Biosci. Biotechnol. Biochem.* 59:2336-2338). Additional selectable markers include, for example, a mutant EPSPV-synthase, which confers glyphosate resistance (Hinchee et al., (1998) *BioTechnology* 91:915-922), a mutant acetolactate synthase, which confers imidazolinone or sulfonylurea resistance (Lee et al., (1988) *EMBO J.* 7:1241-1248), a mutant psbA, which confers resistance to atrazine (Smeda et al., (1993) *Plant Physiol.* 103:911-917), or a mutant protoporphyrinogen oxidase (see U.S. Pat. No. 5,767,373), or other markers conferring resistance to an herbicide such as glufosinate. Examples of suitable selectable marker genes include, but are not limited to, genes encoding resistance to chloramphenicol (Herrera Estrella et al., (1983) *EMBO J.* 2:987-992); streptomycin (Jones et al., (1987) *Mol. Gen. Genet.* 210:86-91); spectinomycin (Bretagne-Sagnard et al., (1996) *Transgenic Res.* 5:131-137); bleomycin (Hille et al., (1990) *Plant Mol. Biol.* 7:171-176); sulfonamide (Guerineau et al., (1990) *Plant Mol. Biol.* 15:127-136); bromoxynil (Stalker et al., (1988) *Science* (1986) 242:419-423); glyphosate (Shaw et al., *Science* 233:478-481); phosphinothricin (DeBlock et al., (1987) *EMBO J.* 6:2513-2518), and the like. One option for use of a selective gene is a glufosinate-resistance encoding DNA and in one embodiment can be the phosphinothricin acetyl transferase (PAT), maize optimized PAT gene or bar gene under the control of the CaMV 35S or ubiquitin promoters. The genes confer resistance to bialaphos. See, Gordon-Kamm et al., (1990) *Plant Cell* 2:603; Uchimiya et al., (1993) *BioTechnology* 11:835; White et al., *Nucl. Acids Res.* 18:1062, (1990); Spencer et al., 1990) *Theor. Appl. Genet.* 79:625-631, and Anzai et al., (1989) *Mol. Gen. Gen.* 219:492. A version of the PAT gene is the maize optimized PAT gene, described at U.S. Pat. No. 6,096,947.

In addition, markers that facilitate identification of a cell containing the polynucleotide encoding the marker may be employed. Scorable or screenable markers are useful, where presence of the sequence produces a measurable product and can produce the product without destruction of the cell. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. (1987) *The EMBO Journal* vol. 6 No. 13 pp. 3901-3907); alkaline phosphatase. Other screenable markers include the anthocyanin/flavonoid genes in general (See discussion at Taylor and Briggs, (1990) *The Plant Cell* 2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize C1 gene (Kao et al., (1996) *Plant Cell* 8: 1171-1179; Scheffler et al. (1994) *Mol. Gen. Genet.* 242:40-48) and maize C2 (Wienand et al., (1986) *Mol. Gen. Genet.* 203:202-207); the B gene (Chandler et al., (1989) *Plant Cell* 1:1175-1183), the p1 gene (Grotewold et al, (1991 *Proc. Natl. Acad. Sci. USA*) 88:4587-4591; Grotewold et al., (1994) *Cell* 76:543-553; Sidorenko et al., (1999) *Plant Mol. Biol.* 39:11-19); the bronze locus genes (Ralston et al., (1988) *Genetics* 119:185-197; Nash et al., (1990) *Plant Cell* 2(11): 1039-1049), among others. Yet further examples of suitable markers include the cyan fluorescent protein (CYP) gene (Bolte et al. (2004) *J. Cell Science* 117: 943-54 and Kato et al. (2002) *Plant Physiol* 129: 913-42), the yellow fluorescent protein gene (PhiYFP™ from Evrogen; see Bolte et al. (2004) *J. Cell Science* 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) *EMBO J.* 8:343); a green fluorescent protein (GFP) gene (Sheen et al., (1995) *Plant J.* 8(5):777-84); and DsRed where cells transformed with the marker gene are red in color, and thus visually selectable (Dietrich et al. (2002) *Biotechniques* 2(2):286-293). Additional examples include a p-lactamase gene (Sutcliffe, (1978) *Proc. Nat'l. Acad. Sci. U.S.A.* 75:3737), which encodes an enzyme for which various chromogenic substrates are known (e.g., PADAC, a chromogenic cephalosporin); a xylE gene (Zukowsky et al., (1983) *Proc. Nat'l. Acad. Sci. U.S.A.* 80:1101), which encodes a catechol dioxygenase that can convert chromogenic catechols; an α-amylase gene (Ikuta et al., (1990) *Biotech.* 8:241); and a tyrosinase gene (Katz et al., (1983) *J. Gen. Microbiol.* 129:2703), which encodes an enzyme capable of oxidizing tyrosine to DOPA and dopaquinone, which in turn condenses to form the easily detectable compound melanin. Clearly, many such markers are available to one skilled in the art.

Leader sequences can be included to enhance translation. Various available leader sequences may be substituted or added. Translation leaders are known in the art and include, for example: picornavirus leaders, for example, EMCV leader (encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165 (2):233-8); human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie. (1987) *Nucleic Acids Res.* 15(8):3257-73); and maize chlorotic mottle virus leader (MCMV) (Lommel et al. (1991) *Virology* 81:382-385). See also, Della-Cioppa et al. (1987) *Plant Physiology* 84:965-968.

The expression vector can optionally also contain a signal sequence located between the promoter and the gene of interest and/or after the gene of interest. A signal sequence is a nucleotide sequence, translated to give an amino acid sequence, which is used by a cell to direct the protein or polypeptide of interest to be placed in a particular place within or outside the eukaryotic cell. Many signal sequences are known in the art. See, for example Becker et al., (1992) *Plant Mol. Biol.* 20:49, Knox, C., et al., "Structure and Organization of Two Divergent Alpha-Amylase Genes from Barley", *Plant Mol. Biol.* 9:3-17 (1987), Lerner et al., (1989) *Plant Physiol.* 91:124-129, Fontes et al., (1991) *Plant Cell* 3:483-496, Matsuoka et al., (1991) *Proc. Natl. Acad. Sci.* 88:834, Gould et al., (1989) *J. Cell. Biol.* 108:1657, Creissen et al., (1991) *Plant J.* 2:129, Kalderon, et al., (1984) "A short amino acid sequence able to specify nuclear location," *Cell* 39:499-509, Steifel, et al., (1990) "Expression of a maize cell wall hydroxyproline-rich glycoprotein gene in early leaf and root vascular differentiation" *Plant Cell* 2:785-793. When targeting the protein to the cell wall use of a signal sequence is necessary. One example is the barley alpha-amylase signal sequence. Rogers, J. C. (1985) "Two barley alpha-amylase gene families are regulated differently in aleurone cells" *J. Biol. Chem.* 260: 3731-3738.

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, *Zea mays* Brittle-1 chloroplast transit peptide (Nelson et al. *Plant Physiol* 117(4):1235-1252 (1998); Sullivan et al. *Plant Cell* 3(12):1337-48; Sullivan et al., *Planta* (1995) 196(3):477-84; Sullivan et al., *J. Biol. Chem.* (1992) 267 (26):18999-9004) and the like. One skilled in the art will readily appreciate the many options available in expressing a product to a particular organelle. Use of transit peptides is well known (e.g., see U.S. Pat. Nos. 5,717,084; 5,728,925). A protein may be targeted to the endoplasmic reticulum of the plant cell. This may be accomplished by use of a localization sequence, such as KDEL. This sequence (Lys-Asp-Glu-Leu) contains the binding site for a receptor in the endoplasmic reticulum. (Munro et al., (1987) "A C-terminal signal prevents secretion of luminal ER proteins." *Cell.* 48:899-907. Retaining the protein in the vacuole is another example. Signal sequences to accomplish this are well known. For example, Raikhel U.S. Pat. No. 5,360,726 shows a vacuole signal sequence as does Warren et al at U.S. Pat. No. 5,889,174. Vacuolar targeting signals may be present either at the amino-terminal portion, (Holwerda et al., (1992) *The Plant Cell,* 4:307-318, Nakamura et al., (1993) *Plant Physiol.,* 101:1-5), carboxy-terminal portion, or in the internal sequence of the targeted protein. (Tague et al., (1992) *The Plant Cell,* 4:307-318, Saalbach et al. (1991) *The Plant Cell,* 3:695-708). Additionally, amino-terminal sequences in conjunction with carboxy-terminal sequences are responsible for vacuolar targeting of gene products (Shinshi et al. (1990) *Plant Molec. Biol.* 14:357-368).

In addition to a promoter, the expression cassette can include one or more enhancers. By "enhancer" is intended a cis-acting sequence that increases the utilization of a promoter. Such enhancers can be native to a gene or from a heterologous gene. Further, it is recognized that some promoters can contain one or more enhancers or enhancer-like elements. An example of one such enhancer is the 35S enhancer, which can be a single enhancer, or duplicated. See for example, McPherson et al, U.S. Pat. No. 5,322,938. Other methods known to enhance translation can also be utilized, for example, introns, and the like. Other modifications can improve expression, include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The termination region can be native with the promoter nucleotide sequence can be native with the DNA sequence of interest, or can be derived from another source. Convenient termination regions are available from the Ti-plasmid of *A. tumefaciens*, such as the octopine synthase (MacDonald et al., (1991) *Nuc. Acids Res.* 19(20)5575-5581) and nopaline synthase termination regions (Depicker et al., (1982) *Mol. and Appl. Genet.* 1:561-573 and Shaw et al. (1984) *Nucleic Acids Research Vol.* 12, No. 20 pp 7831-7846 (nos)). Examples of various other terminators include the pin II terminator from the protease inhibitor II gene from potato (An, et al. (1989) *Plant Cell* 1, 115-122. See also, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Obviously, many variations on the promoters, selectable markers, signal sequences, leader sequences, termination sequences, introns, enhancers and other components of the vector are available to one skilled in the art.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions, such as transitions and transversions, can be involved.

The transformation vector comprising the sequence operably linked to a heterologous nucleotide sequence in an expression cassette, can also contain at least one additional nucleotide sequence for a gene to be cotransformed into the organism. Alternatively, the additional sequence(s) can be provided on another transformation vector.

The method of transformation/transfection is not critical; various methods of transformation or transfection are currently available. As newer methods are available to transform crops or other host cells they may be directly applied. Accordingly, a wide variety of methods have been developed to insert a DNA sequence into the genome of a host cell to obtain the transcription or transcript and translation of the sequence to effect phenotypic changes in the organism. Thus, any method which provides for efficient transformation/transfection may be employed.

Methods for introducing expression vectors into plant tissue available to one skilled in the art are varied and will depend on the plant selected. Procedures for transforming a wide variety of plant species are well known and described throughout the literature. (See, for example, Miki and McHugh (2004) *Biotechnol.* 107, 193-232; Klein et al. (1992) *Biotechnology* (N Y) 10, 286-291; and Weising et al. (1988) *Annu. Rev. Genet.* 22, 421-477). For example, the DNA construct may be introduced into the genomic DNA of the plant cell using techniques such as microprojectile-mediated delivery (Klein et al. 1992, supra), electroporation (Fromm et al., 1985 *Proc. Natl. Acad. Sci. USA* 82, 5824-5828), polyethylene glycol (PEG) precipitation (Mathur and Koncz, 1998 *Methods Mol. Biol.* 82, 267-276), direct gene transfer (WO 85/01856 and EP-A-275 069), in vitro protoplast transformation (U.S. Pat. No. 4,684,611), and microinjection of plant cell protoplasts or embryogenic callus (Crossway, A. (1985) *Mol. Gen. Genet.* 202, 179-185). *Agrobacterium* transformation methods of Ishida et al. (1996) and also described in U.S. Pat. No. 5,591,616 are yet another option. Co-cultivation of plant tissue with *Agrobacterium tumefaciens* is a variation, where the DNA constructs are placed into a binary vector system (Ishida et al., 1996 *Nat. Biotechnol.* 14, 745-750). The virulence functions of the *Agrobacterium tumefaciens* host will direct the insertion of the construct into the plant cell DNA when the cell is infected by the bacteria. See, for example, Fraley et al. (1983) *Proc. Natl. Acad. Sci. USA,* 80, 4803-4807. *Agrobacterium* is primarily used in dicots, but monocots including maize can be transformed by *Agrobacterium*. See, for example, U.S. Pat. No. 5,550,318. In one of many variations on the method, *Agrobacterium* infection of corn can be used with heat shocking of immature embryos (Wilson et al. U.S. Pat. No. 6,420,630) or with antibiotic selection of Type II callus (Wilson et al., U.S. Pat. No. 6,919,494).

Rice transformation is described by Hiei et al. (1994) *Plant J.* 6, 271-282 and Lee et al. (1991) *Proc. Nat. Acad. Sci. USA* 88, 6389-6393. Standard methods for transformation of canola are described by Moloney et al. (1989) *Plant Cell Reports* 8, 238-242. Corn transformation is described by Fromm et al. (1990) *Biotechnology* (N Y) 8, 833-839 and Gordon-Kamm et al. (1990) supra. Wheat can be transformed by techniques similar to those used for transforming corn or rice. Sorghum transformation is described by Casas et al. (Casas et al. (1993) Transgenic sorghum plants via microprojectile bombardment. *Proc. Natl. Acad. Sci. USA* 90, 11212-11216) and barley transformation is described by Wan and Lemaux (Wan and Lemaux (1994) Generation of large numbers of independently transformed fertile barley plants. *Plant Physiol.* 104, 37-48). Soybean transformation is described in a number of publications, including U.S. Pat. No. 5,015,580.

In one method, the *Agrobacterium* transformation methods of Ishida et al. (1996) and also described in U.S. Pat. No. 5,591,616, are generally followed, with modifications that the inventors have found improve the number of transformants obtained. The Ishida method uses the A188 variety of maize that produces Type I callus in culture. In an embodiment the Hi II maize line is used which initiates Type II embryogenic callus in culture (Armstrong et al., 1991).

While Ishida recommends selection on phosphinothricin when using the bar or pat gene for selection, another preferred embodiment provides use of bialaphos instead. In general, as set forth in the U.S. Pat. No. 5,591,616, and as outlined in more detail below, dedifferentiation is obtained by culturing an explant of the plant on a dedifferentiation-inducing medium for not less than seven days, and the tissue during or after dedifferentiation is contacted with *Agrobacterium* having the gene of interest. The cultured tissue can be callus, an adventitious embryo-like tissue or suspension cells, for example. In this preferred embodiment, the suspension of *Agrobacterium* has a cell population of $10^6$ to $10^{11}$ cells/ml and are contacted for three to ten minutes with the tissue, or continuously cultured with *Agrobacterium* for not less than seven days. The *Agrobacterium* can contain plasmid pTOK162, with the gene of interest between border sequences of the T region of the plasmid, or the gene of interest may be present in another plasmid-containing *Agrobacterium*. The virulence region may originate from the virulence region of a Ti plasmid or Ri plasmid. The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, but not an *Agrobacterium* replication origin, it cannot survive in *Agrobacterium* without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA101, selecting for spectinomycin resistance. The plasmid is isolated to assure that the EHA101 contains the plasmid. EHA101 contains a disarmed pTi that carries resistance to kanamycin. See, Hood et al. (1986).

Further, the Ishida protocol as described provides for growing fresh culture of the *Agrobacterium* on plates, scraping the bacteria from the plates, and resuspending in the co-culture medium as stated in the U.S. Pat. No. 5,591,616 for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose and 36 g glucose per liter, all at a pH of 5.8. In a further preferred method, the bacteria are grown overnight in a 1 ml culture and then a fresh 10 ml culture is re-inoculated the next day when transformation is to occur. The bacteria grow into log phase, and are harvested at a density of no more than $OD_{600}=0.5$, preferably between 0.2 and 0.5. The bacteria are then centrifuged to remove the media and resuspended in the co-culture medium. Since Hi II is used, medium preferred for Hi II is used. This medium is described in considerable detail by Armstrong and Green (1985). The resuspension medium is the same as that described above. All further Hi II media are as described in Armstrong and Green (1985). The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

A transgenic plant may be produced that contains an introduced nucleic acid molecule encoding the membrane-bound polypeptide.

When referring to introduction of a nucleotide sequence into a plant is meant to include transformation into the cell, as well as crossing a plant having the sequence with another plant, so that the second plant contains the heterologous sequence, as in conventional plant breeding techniques. Such breeding techniques are well known to one skilled in the art. This can be accomplished by any means known in the art for breeding plants such as, for example, cross pollination of the transgenic plants that are described above with other plants, and selection for plants from subsequent generations which express the amino acid sequence. The plant breeding methods used herein are well known to one skilled in the art. For a discussion of plant breeding techniques, see Poehlman (1995) *Breeding Field Crops*. AVI Publication Co., Westport Conn., $4^{th}$ Edit.). Many crop plants useful in this method are bred through techniques that take advantage of the plant's method of pollination. A plant is self-pollinating if pollen from one flower is transferred to the same or another flower of the same plant. A plant is cross-pollinating if the pollen comes from a flower on a different plant. For example, in *Brassica*, the plant is normally self-sterile and can only be cross-pollinated unless, through discovery of a mutant or through genetic intervention, self-compatibility is obtained. In self-pollinating species, such as rice, oats, wheat, barley, peas, beans, soybeans, tobacco and cotton, the male and female plants are anatomically juxtaposed. During natural pollination, the male reproductive organs of a given flower pollinate the female reproductive organs of the same flower. Maize plants (*Zea mays* L.) can be bred by both self-pollination and cross-pollination techniques. Maize has male flowers, located on the tassel, and female flowers, located on the ear, on the same plant. It can self or cross-pollinate.

Pollination can be by any means, including but not limited to hand, wind or insect pollination, or mechanical contact between the male fertile and male sterile plant. For production of hybrid seeds on a commercial scale in most plant species pollination by wind or by insects is preferred. Stricter control of the pollination process can be achieved by using a variety of methods to make one plant pool male sterile, and the other the male fertile pollen donor. This can be accomplished by hand detas sling, cytoplasmic male sterility, or control of male sterility through a variety of methods well known to the skilled breeder. Examples of more sophisticated male sterility systems include those described by Brar et al., U.S. Pat. Nos. 4,654,465 and 4,727,219 and Albertsen et al., U.S. Pat. Nos. 5,859,341 and 6,013,859.

Backcrossing methods may be used to introduce the gene into the plants. This technique has been used for decades to introduce traits into a plant. An example of a description of this and other plant breeding methodologies that are well known can be found in references such as Neal (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

Any plant species may be used, whether monocotyledonous or dicotyledonous, including but not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus*

*casica*), guava (*Psidium guajava*), mango (*Mangifera indica*), olive (*Olea europaea*), papaya (*Carica papaya*), cashew (*Anacardium occidentale*), *macadamia* (*Macadamia integrifolia*), almond (*Prunus amygdalus*), sugar beets (*Beta vulgaris*), oats (Avena), barley (Hordeum), vegetables, ornamentals, and conifers. Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.) and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers which may be employed in practicing the present invention include, for example, pines such as loblolly pine (*Pinus taeda*), slash pine (*Pinus elliotii*), ponderosa pine (*Pinus ponderosa*), lodgepole pine (*Pinus contotta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

The following is provided by way of illustration of the invention and is not intended to limit the scope of the invention.

EXAMPLE 1

Preparation of Construct

The Hepatitis B surface antigen (HBsAg) sequence, identical to the surface antigen protein sequence available in GenBank accession 562754.1 (adr subtype, small form i.e. S open reading frame without pre-S1 or pre-S2 sequences), was engineered to be codon optimized for expression in maize. See FIG. 1 where the HBsAg optimized sequence is SEQ ID NO: 2 and indicated in regular font with the ATG translation start site in bold italics. At the N-terminus is a cell-wall targeting sequence, the barley alpha amylase signal sequence, shown in italics and which is SEQ ID NO: 3. (Rogers, J. C. (1985) "Two barley alpha-amylase gene families are regulated differently in aleurone cells" *J. Biol. Chem.* 260, 3731 3738). The BAASS sequence was fused to HBsAg in order to produce maximally-expressing lines. All HBsAg constructs were built to contain a Pin II (potato proteinase inhibitor II) termination sequence. See An, et al. (1989) "Functional analysis of the 3' control region of the potato wound-inducible proteinase inhibitor II gene" *Plant Cell* 1, 115 122. The globulin-1 regulatory region of Belanger et al., supra, of GenBank accession No. L22344 (shown in FIG. 2 in lower case text, SEQ ID NO: 4) was used, followed by an extra 43 bases (shown in FIG. 2 in upper case italics, SEQ ID NO: 11). These extra bases are not relevant to the regulatory region and are believed to be a portion of chromosome 1 of the maize gene, which may originate from a retrotransposon. A selectable marker employed in the construct is the maize optimized PAT sequence providing resistance to the herbicide glufosinate. See, Gordon-Kamm et al., (1990) *Plant Cell* 2:603; Uchimiya et al., (1993) *BioTechnology* 11:835; White et al., *Nucl. Acids Res.* 18:1062, (1990); Spencer et al., (1990) *Theor. Appl. Genet.* 79:625-631, and Anzai et al., (1989) *Mol. Gen. Gen.* 219:492. A version of the PAT gene is the maize optimized PAT gene, described in U.S. Pat. No. 6,096,947.) The resulting plasmid HBE map is shown in FIG. 3. HBG was constructed using the extended globulin-1 promoter of U.S. Pat. No. 7,169,967, incorporated herein by reference and see FIG. 5. The nucleotide sequence used here (SEQ ID NO: 10) is the same as that of the '967 patent, with one base change at 3003 of FIG. 5, the base directly preceding the ATG start codon where a C instead of a G was used (to incorporate the NcoI restriction site at the start codon). See FIG. 4 for the plasmid map. Two plant transcription units (PTUs), each consisting of a promoter, protein coding sequence, and termination sequence, were placed one next to the other such that 190 bp of sequence separated the end of the first PTU's termination sequence and the beginning of the next PTU's promoter sequence. This was achieved by cutting the HBF vector (here, FIG. 6) in two separate reactions. The first reaction cut with PmeI to linearize the vector. The second reaction cut with PmeI and NheI and the NheI 5' overhang was filled in using a Klenow fragment. This second fragment consisted of spacer DNA sequence, the extended globulin promoter, the HBsAg coding sequence, and the PinII termination sequence. The PmeI/filled NheI fragment was inserted into the linearized vector's PmeI site using a blunt end ligation and the orientation of the fragment was screened using restriction fragment analysis. This resulted in a two PTU vector.

EXAMPLE 2

Transformation and Assays

The HBE construct was transformed into maize plants using an *Agrobacterium tumefaciens* superbinary vector transformation system. *Zea mays* was used as the host plant and regeneration of plants were conducted in growth chambers and greenhouses to generate $T_0$ plants producing $T_1$ seed. Expression levels for HBE $T_1$ seed were assayed using a sandwich ELISA protocol as briefly described below:

Extraction of HBsAg from seed: 100 mg of ground seed samples were agitated in 1 mL of extraction buffer (PBS with 1% Triton X-100) with a ball bearing at 600 oscillations per minute for 20 seconds, centrifuged, and the supernatant diluted and applied to the ELISA plate. ELISA assay for HBsAg on 96-well plate: Rabbit anti-HBsAg antibody was used to coat 96-well plates, corn extracts were added to the coated plates, followed by biotinylated rabbit anti-HBsAg, streptavidin conjugated to alkaline phosphatase, and finally pNPP substrate. Washes were conducted between each step using PBST and blocking solution was 3% BSA in PBST.

EXAMPLE 3

Preparation of HBsAg Expressing Lines

All defatting work was done with material derived from HBE lines. HBE lines used:

CC090013)1: HBE $T_0$ plants were backcrossed 3 times to SP122 and selfed twice to produce a homozygous line. Seed from the second self were tested for homozygosity using herbicide screening (100% resistance). These plants were grown to maturity and selfed to produce the CC090013)1 seed. The ground seed was then used as a positive control for the ELISA assays.

CC100054]1: HBE $T_0$ plants were backcrossed 6 times to SP114 and selfed once to produce seed for defatting experiments. Whole seed and germ were used for defatting experiments. Germ was extracted from the seed by soaking them in water overnight and hand dissecting the embryo (germ). The germ was then dried overnight at 37° C. to a moisture content of 6-15%.

EXAMPLE 4

Effect of Fat Addition and Fat Reduction on Antibody Detection of HBsAg

Germ and seed of the lines prepared as above were ground in a coffee grinder to the texture of fine cornmeal.

CC100054]1 ground material was defatted using a hexane treatment or a supercritical fluid extraction (SFE) treatment. For hexane treatment, a total of 5 mL of hexane was added to every 1 g of seed or germ material. For SFE treatment, ground germ was defatted using a constant $CO_2$ flow of 20 g/min, at 350 bar, and 35° C. in the extraction chamber. Conditions were maintained until oil was no longer exiting the waste chamber.

Oil or butter was added to the ground plant material as indicated in the table below.

Extraction of the HBsAg from the ground seed was done as described above, with various extraction buffers (see table below "Extraction Conditions" for details). The concentration of HBsAg in seed and germ was determined using a sandwich ELISA as described above.

It was initially observed that adding 80 uL melted butter to 100 mg ground germ or seed or adding 50 to 80 uL canola oil to 100 mg germ was associated with decreased detection of HBsAg compared to ground germ or seed where oil or butter was not added. Tests were then conducted on defatting ground germ and seed. Results are summarized below.

TABLE 2

Ground seed

| Sample | Extraction conditions | Median HBsAg (ng/uL) | Data source |
|---|---|---|---|
| CC100054]1 seed | PBS + 0.05% Tween | 0.03 | HepB_CH029 |
| CC100054]1 hexane defatted seed | | 0.11 | |
| CC100054]1 seed | PBS + 0.1% Triton X-100 | 1.42 | HepB_CH029 |
| CC100054]1 hexane defatted seed | | >3 | |

TABLE 3

Ground germ

| Sample | Conditions | Extraction conditions | Median HBsAg (ng/uL) | Data source |
|---|---|---|---|---|
| CC100054]1 fullfat germ | No oil/ butter | PBS + 0.1% Triton X-100 | 4.52 | HepB_CH028 |
| CC100054]1 hexane defatted germ | | | 7.43 | |
| CC100054]1 fullfat germ | No oil/ butter | PBS + 0.05% Tween | 0.27 | HepB_CH029 |
| CC100054]1 hexane defatted germ | | | 0.34 | |

TABLE 3-continued

Ground germ

| Sample | Conditions | Extraction conditions | Median HBsAg (ng/uL) | Data source |
|---|---|---|---|---|
| CC100054]1 fullfat germ | No oil/ butter | PBS + 0.1% Triton X-100 | 1.89 | HepB_CH029 |
| CC100054]1 hexane defatted germ | | | 6.47 | |

The inventors concluded there was an association between reducing fat content of the plant material and increased detection of the membrane-bound protein.

EXAMPLE 5

Antibody Production in Animals in Response to Administration of Plant Produced HBsAg In an initial experiment (mouse trial #1), whole, full-fat HBE seed was used to produce HBsAg expressing germ and was fed to mice, but an anti-HBsAg immune response could not be detected when compared to whole, full-fat control germ. The seed was soaked and degermed by hand. The germ was maintained at about 50% moisture and stored in the −80° C. freezer and thawed just prior to feeding the mice. Mice were initially injected with 1.0 ug RECOMBIVAX® (commercial HBsAg vaccine) and at nine weeks post-injection fed a first boosting dose consisting of 5 g of whole germ on each of three consecutive days. A total of 3 oral boosts were administered, each 2 weeks apart.

The following experimentation used HBE seed and demonstrated that reducing oil in plant material provided for an immune response.

Mouse Trial #2

Grain containing the HBE construct was collected and degermed by soaking the seed in water 1-3 days and hand dissecting the germ from the endosperm using pliers. Dissected germ was dried in a 37° C. incubator to 6-15% moisture. Germ from transgenic lines as well as a non-transgenic line (control germ) was then ground using a coffee grinder to a fine cornmeal consistency. Both control and HBsAg germ were defatted using a hexane extraction. Every 1 gram of ground germ was extracted with 5 mL of hexane. Residual hexane was removed from the germ by evaporation at room temperature over 1-3 days. All hexane extracted germ batches were thoroughly mixed to create a homogenous antigen concentration.

Figure 7:
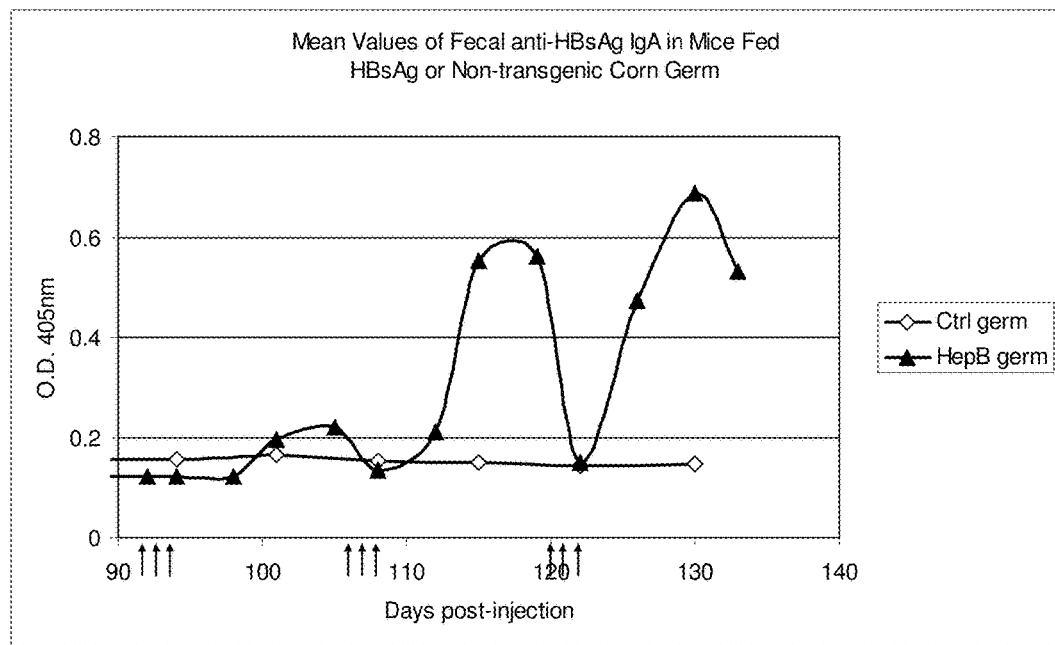
FIG. 7 is a graph summarizing the antibody response to mouse feeding trials. Arrows point to days of oral boosting.

Balb/c mice were injected with 0.5 μg of RECOMBIVAX®, a commercially available Hepatitis B vaccine, on Day 0. HBsAg or control germ were fed to mice 14 weeks post-injection. Mice received three oral boost doses each two weeks apart. Each oral boost consisted of three 5 g doses administered over three consecutive days (Days 92, 93, 94, 106, 107, 108, 120, 121, 122). The final % TSP in the ground germ was approximately 0.2%, therefore mice were fed approximately 0.6 mg of HBsAg per 5 g oral dose. Fecal samples were collected at the time of initial injection, and then every two weeks following oral boost doses (Days 0, 92, 94, 98, 101, 105, 108, 112, 115, 119, 122, 126, 129, and 133). IgA was detected using an ELISA. Briefly, HBsAg was used to coat ELISA plates. Plates were subsequently incubated with fecal samples (100 mg resuspended in 1 mL of 1×PBS+1% BSA+ protease inhibitor), an anti-mouse IgA antibody conjugated to alkaline phosphatase, and a pNPP solution. Reaction O.D.s were read at 405 nm. Results are summarized in FIG. 7. Arrows indicate the oral boost days. With each oral boost, a progressively stronger IgA induction was seen. This established that defatted HBsAg plant material can induce a strong immune response in mice.

Figure 8:
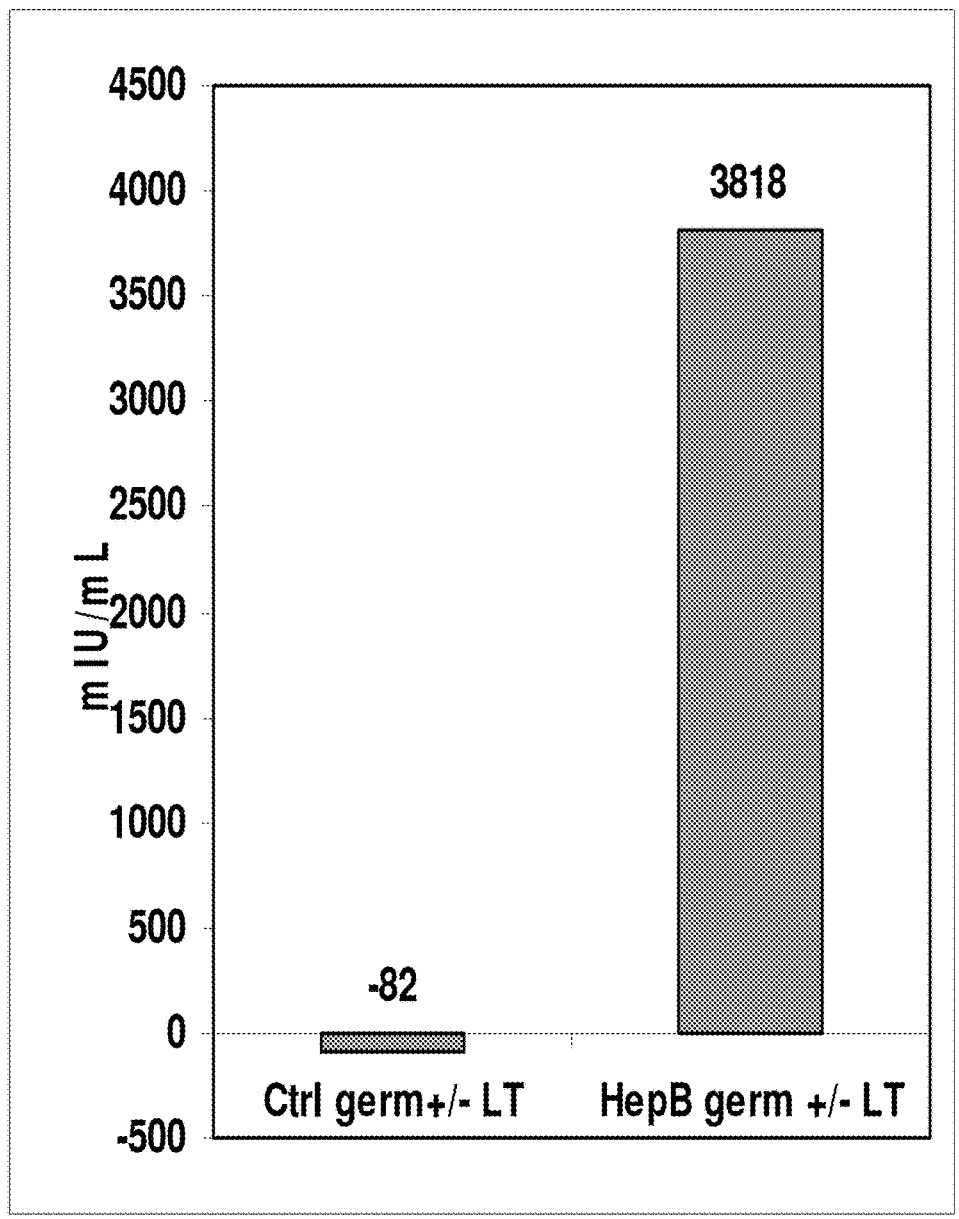
FIG. 8 is a graph showing comparison of serum response titer in mice after administration of two boosting doses of control germ with or without heat-labile enterotoxin LT and two boosting doses of germ expressing HBsAg with or without LT.
Figure 9:
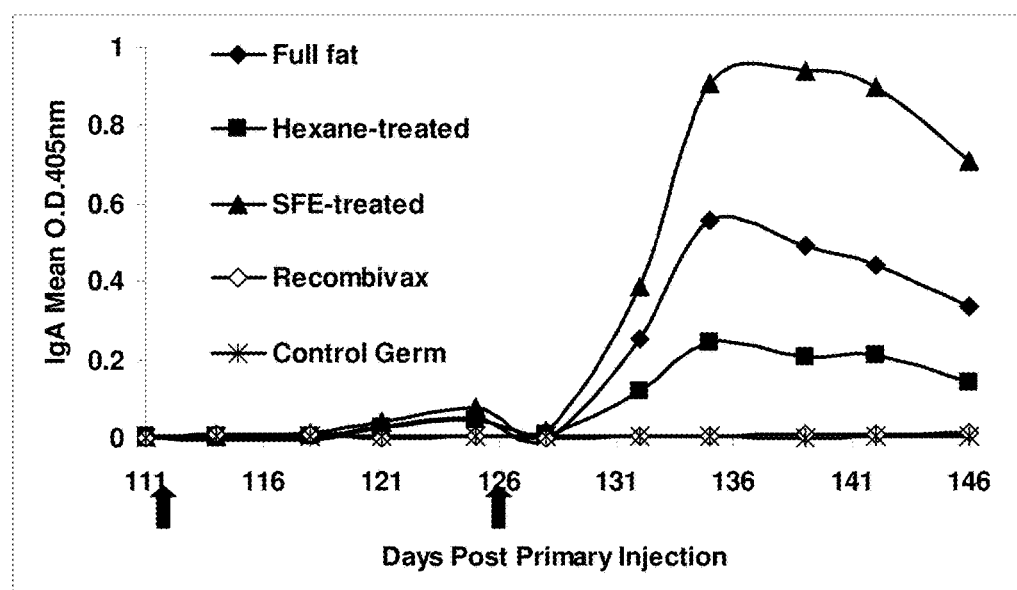
FIG. 9 is a graph showing the fecal IgA antibody response to HBsAg boosting in mice as determined by sandwich ELISA. Arrows point to days of boosting, either by oral route or by injection with RECOMBIVAX®.
Figure 10:
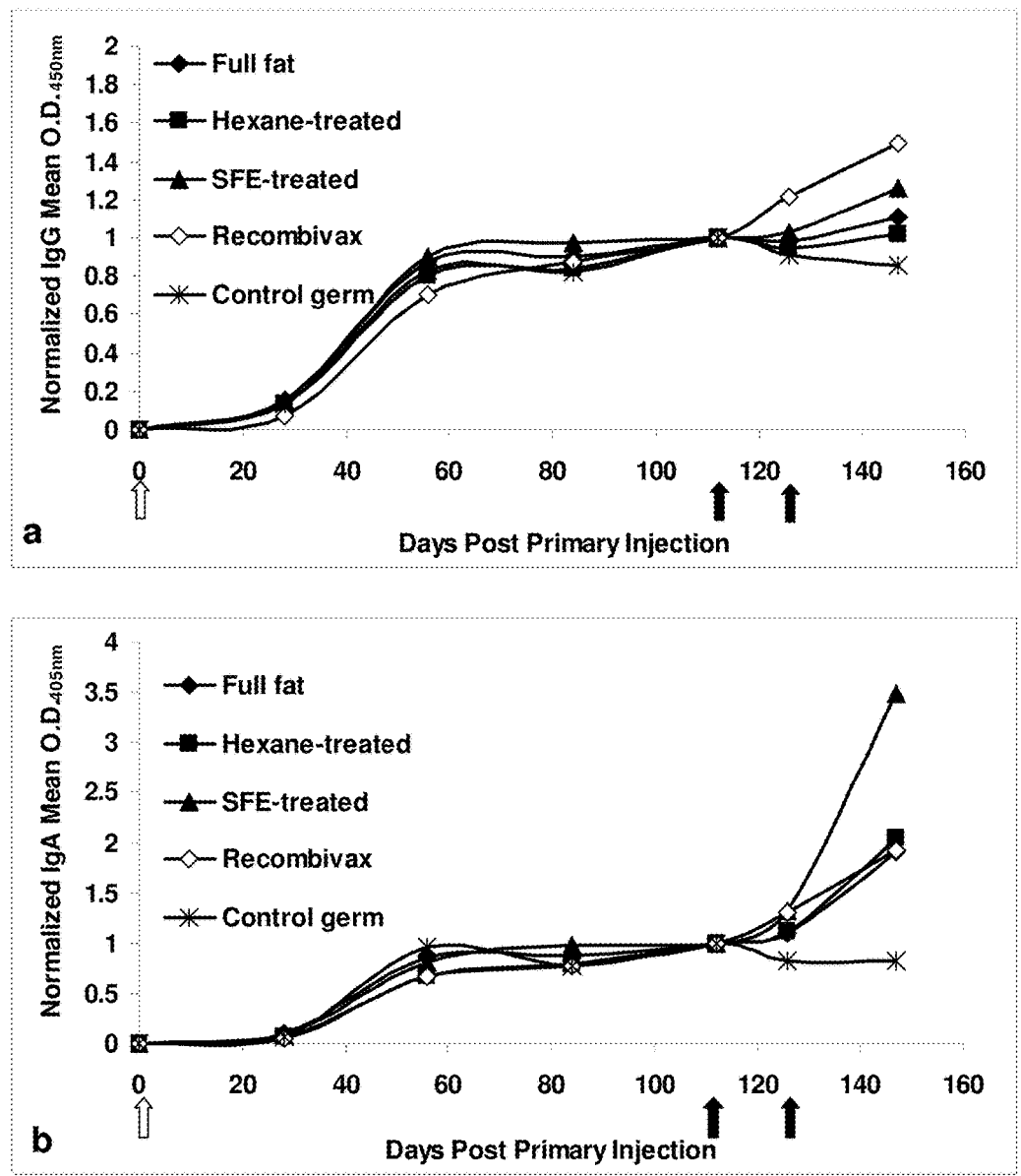
FIG. 10 shows two graphs showing serum IgG (11A) and IgA (11B) response in mouse feeding trials as determined by sandwich ELISA. The white arrow indicates primary injection of RECOMBIVAX® and the black arrows indicate initiation of oral boosting or RECOMBIVAX® injection.

The control germ was also tested with heat-labile enterotoxin LT and HepB germ with LT, which did not cause any remarkable variations in results. The serum response was also examined and mice produced a 3800 mIU/mL mean increase in titer after boosting with HBsAg germ (FIG. 8). Seroconversion in humans using the WHO international standard is considered to be a protective response with titers greater than 10 mIU/mL (Zuckerman, et al. (1997) "Immune response to a new hepatitis B vaccine in healthcare workers who had not responded to standard vaccine: randomized double blind dose-response study" BMJ 314, 329). Therefore, using this non-optimized maize material, a convincing immune response was observed. Furthermore, this response was obtained without an adjuvant and is 3 to 4-fold greater compared to the earlier potato study (Kong, et al. (2001) "Oral immunization with hepatitis B surface antigen expressed in transgenic plants" *Proc Natl Acad Sci USA* 98, 11539-115) which did use an adjuvant. In human clinical trials, the HBsAg maize material should therefore potentiate a robust response in a much larger proportion of volunteers than the potato material (Thanavala, et al. (2005) "Immunogenicity in humans of an edible vaccine for hepatitis B" *Proc Natl Acad Sci USA* 102, 3378-3382).

EXAMPLE 6

Mouse Trial #3

Several methods can be used to remove oil such as supercritical fluid extraction (SFE) or hexane extraction. SFE (Brunner, G. (2005) Supercritical fluids: technology and application to food processing, *Journal of Food Engineering* 67, 21-33) was explored which is food friendly using only carbon dioxide ($CO_2$) for oil extraction. Mouse trials indicate that the SFE-treated maize material can elicit a superior immunologic response compared to the hexane-treated material.

Maize Material

All maize material used for the mouse study was derived from seed containing the HBG construct, as previously described supra and at Hayden et al. (2012) *Plant Biotechnology Journal*, 10, pp. 979-984. All maize material used in the mouse studies was hybrid grain derived from heterozygous plants that contained genetic background from elite parent inbred lines 16038 and MBS5411. Control germ was G909 germ from the Grain Processing Corporation (Muscatine, Iowa).

Seed Processing

HBG hybrid seed was soaked for 5 days in water to approximately 50% moisture, germ was extracted by hand, dried overnight at 37° C. to a final moisture of 6-15%, and ground to a fine cornmeal consistency. Ground germ was defatted by either hexane extraction or supercritical fluid extraction (SFE). Hexane extractions were conducted as previously described (Hayden et al, 2012, *Plant Biotechnology Journal*, supra). Briefly, a total of 5 mL of hexane over three extractions was used for every gram of ground maize material. Samples were vigorously mixed for 15 min during each extraction and filtered through No. 1 Whatman filter paper using a Buchner funnel at room temperature. Samples were dried in a fume hood to remove residual hexane. SFE treatment consisted of $CO_2$ extraction at 350 bar, 40-53° C. vessel temperature, using a 5 L vessel in an SFT-250 (Supercritical Fluid Technologies, Newark, Del.).

Wafer Processing

Wafers were made for oral mouse feedings. Because defatting of the material can concentrate the HBsAg in maize material significantly, germ expressing HBsAg was then blended with control germ (either full fat, hexane-treated, or SFE-treated) to obtain approximately equivalent concentrations of HBsAg in all germ parent material used to make wafers. Control wafers were made with SFE-treated control germ. Each wafer contained 2.5 g germ flour and 0.65 g of ultrafine baker's sugar (C&H). Water was added to give a moldable consistency that was 15% of the germ weight for full fat material, and 25% for SFE- and hexane-defatted material. Wafers were hand-pressed into circular plastic molds (cat#40116, Decagon/AquaLab, Pullman, Wash.) and dried in a VWR 1430 vacuum oven (VWR Scientific, Radnor, Pa.) at 58-62° C., 21-22" Hg until wafers lost >90% of the added water.

Antigen Detection

To test HBsAg antigen levels in ground maize material or wafers 100 mg samples were weighed out in duplicate and each sample was extracted in 1 mL PBS+1% TritonX-100. Four wafers were tested per treatment. HBsAg was assayed by sandwich ELISA using 1:1000 diluted extracts in triplicate, and using a monoclonal capture antibody (cat#C01246M, Meridian Life Sciences, Memphis, Tenn.), and a polyclonal HRP-conjugated detection antibody (cat#B65811P, Meridian Life Sciences).

Mouse Study

BALB/c inbred mice (Harlan) were randomly assigned to treatments 1 through 6 and housed individually. Eleven mice were assigned to treatments 1 through 3 and ten mice were assigned to treatments 4 and 5. All treatments, except treatment 6, were injected with 0.5 µg of RECOMBIVAX® (Merck, Whitehouse Station, N.J.) on day 0, and were boosted with full fat wafers, hexane-defatted wafers, SFE-defatted wafers, RECOMBIVAX®, or control wafers (treatments 1, 2, 3, 4, and 5, respectively), with boosting initiated on day 112 and day 126 post-primary injection. For each boost, two wafers were offered per day for three consecutive days or a single 0.5 µg intra-muscular RECOMBIVAX® injection was administered on the first day. Treatment 6 consisted of 5 mice which were injected with 0.9% sterile saline on day 0 and boosted with control wafers as above.

Anti-HBsAg Antibody Detection in Mice

Blood samples were collected by submandibular venous puncture every 2-4 weeks, centrifuged to remove red blood cells, and stored in 50% glycerol at −20° C. On boosting days, serum was collected a few hours prior to boosting. Fecal material was collected from cages that were cleaned 24 hours prior to sampling, and samples were stored at −20° C. Fecal samples were collected twice a week for the first 5 weeks, and again twice a week starting one day prior to the first boost and ending the week of the terminal bleed. Serum anti-HBsAg IgG and IgA were detected using a sandwich ELISA. Plates were coated with rHBsAg (cat#R86872, Meridian Life Sciences), serum samples diluted 1:250, and HRP-conjugated anti-mouse IgG (cat#ab6789, Abcam, Cambridge, Mass.) or AP-conjugated anti-mouse IgA (cat#ab97232, Abcam) were used to detect IgG and IgA, respectively. For secretory IgA, 100 mg of fecal pellets were resuspended in 1 mL of 1% BSA in PBS containing a protease inhibitor (cat#11836153001, Roche Diagonistics GmbH, Mannheim, Germany) and diluted an additional 1:50 and used in the same assay as the serum samples. For saliva Ig, saliva was collected on day 141 post-primary injection, diluted between 1:5 and 1:25, and detected using the ETI-AB-AUK PLUS assay kit (DiaSorin, Saluggia, Italy) which calculates total anti-HBsAg Ig in mIU/mL based on the WHO $2^{nd}$ International Standard. Serum Ig was also detected using the DiaSorin kit by diluting serum 1:50 or 1:500 so that titers fell on the linear part of the standard curve.

Immunoblot

One hundred milligrams of wafer material was first extracted three times in PBS+0.05% Tween 20 to remove most native corn proteins. A fourth extraction in PBS+0.1% TritonX-100 was then performed to extract HBsAg. Ten microliters of each extract was heated to 100° C. for 10 minutes and run on an SDS-PAGE gel under reducing conditions (50 mM DTT) and analyzed by an immunoblot, as previously described.

Results

Maize lines were backcrossed into elite parental inbred lines and used to produce highly expressing hybrid seed. Germ from hybrid seed showed very high levels of HBsAg, with a mean of 581 μg HBsAg/g germ, the highest reported concentration to date in a plant production system.

HBsAg germ meal from all three samples was mixed with control germ meal that was hexane treated, SFE treated, or untreated to approximate equal concentrations of HBsAg in each type of germ. Germ mixes were then combined with sugar and water, formed into wafers, dried, and HBsAg concentrations determined (Table 4). Based on an ELISA assay, hexane-treated wafers appeared to contain higher concentrations of HBsAg than either full fat or SFE-treated wafers and were more variable in their concentration from wafer to wafer.

TABLE 4

Concentration of HBsAg in wafers as determined by ELISA.

| Sample | Mean [HBsAg] (μg/g wafer) | Std dev |
|---|---|---|
| Full fat wafers | 290 | 40 |
| Hexane-treated wafers | 481 | 93 |
| SFE-treated wafers | 297 | 23 |
| Control wafers | None detected* | |

*Limit of detection is 15 ug/g

To independently assess the relative concentration of HBsAg in the wafers, protein blots were also performed. The protein blot did not indicate that the hexane treated material contained higher concentrations of HBsAg compared to the other treatments. The hexane-treated and full fat wafers seemed to predominantly form a mix of monomeric and dimeric HBsAg under reducing conditions whereas the SFE-treated wafer primarily formed dimeric structures with very little evidence of monomeric molecules.

As with the above experiment, all mice were injected with RECOMBIVAX® except for the last treatment. Two oral boosts were given on days indicated in FIG. 9 by the bold arrows. There was no IgA detected in fecal samples prior to the oral boosts.

TABLE 5

| | Mice responding to treatment | | | | | |
|---|---|---|---|---|---|---|
| Treatment | Strong Response | | Weak Response | | No Response | |
| Full fat germ | 8 | 73% | 1 | 9% | 2 | 18% |
| Hexane treated germ | 7 | 64% | 1 | 9% | 3 | 27% |

TABLE 5-continued

| | Mice responding to treatment | | | | | |
|---|---|---|---|---|---|---|
| Treatment | Strong Response | | Weak Response | | No Response | |
| SFE treated germ | 11 | 100% | 0 | 0% | 0 | 0% |
| RECOMBIVAX ® | 0 | 0% | 0 | 0% | 10 | 100% |
| Control germ | 0 | 0% | 0 | 0% | 10 | 100% |
| No primary or boost | 0 | 0% | 0 | 0% | 6 | 100% |

Mucosal Response to Oral Administration of HBsAg

To test the immunological efficacy of the different germ treatments used in wafer formulations and compare their efficacy relative to a parenteral boosting regime, BALB/c mice were administered 0.5 μg of RECOMBIVAX® as a primary injection at day 0. Mice in the RECOMBIVAX®-boosted treatment received 0.5 μg RECOMBIVAX® on days 112 and 126. Boosting with corn wafers was initiated on these same days and spanned three consecutive days. Treatments included wafers made with full fat, hexane-treated, SFE-treated, and control germ. Two 3.1 g wafers were administered each day which resulted in approximately 5.5 mg of HBsAg being offered during each boost. Mice consumed approximately 75% of the wafers, approximating a 4 mg dose per boost. A sixth treatment consisted of mice receiving saline as a primary injection and control wafers on boosting days. Mice receiving this last treatment showed no immunological response in any of the assays (data not shown).

Secretory IgA in fecal material was strongly induced in all treatments of orally delivered HBsAg while no response was detectable in RECOMBIVAX®-boosted mice or in control wafer fed mice (FIG. 9). Pre-boost data revealed that no response was detected in the first five weeks after primary injection for twelve mice (data not shown). All 11 mice in the SFE wafer treatment group displayed increasing IgA titers after boosting relative to pre-immune titers and more than 70% of mice in full fat and hexane treatments showed increases after the second boost.

With SFE as the extraction method, the antigen is more available to the gut and there is an improved mucosal response, both in the number of mice responding and the degree of response.

The mucosal response to oral boosting was further assessed via secretory IgA in mouse saliva. All SFE-boosted mice that were tested (n=5) showed detectable total Ig levels (O.D. values greater than 4-fold above the highest value recorded for mice fed control wafers), ranging from 2 to 142 mIU/mL. Additionally, O.D. values from RECOMBIVAX®-boosted mice were indistinguishable from control-boosted mice that received either a RECOMBIVAX® primary or a saline primary.

Systemic Response to Oral Administration of HBsAg

Mice were also tested for their systemic response to the oral and injected HBsAg boosting doses. Mouse titers were normalized to their pre-boost levels and post-boost normalized titers were compared (FIG. 10). After boosting, RECOMBIVAX® and SFE-boosted mice showed the highest increase in IgG titers (FIG. 10*a*). Induction of IgA titers after boosting was more pronounced for mice fed SFE-treated wafers, increasing 3.5-fold above pre-boost levels (FIG. 10*b*). Mice fed full fat or hexane-treated material showed comparable mean responses to the RECOMBIVAX® boosted mice, increasing approximately 2-fold above pre-boost levels. Mice fed control germ wafers showed decreasing IgG and IgA titers after boosting, as expected.

Figure 11:
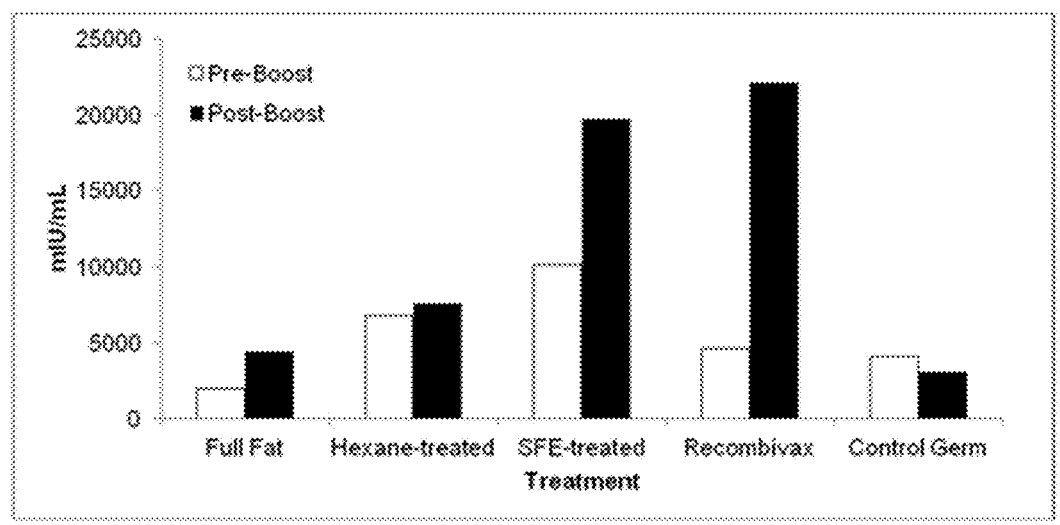
FIG. 11 is a graph showing geometric mean titers of serum anti-HBsAg Ig in mice boosted orally (HBsAg germ or control germ), or parenterally (RECOMBIVAX®). Titers represent samples collected just prior to boosting (pre-boost) and three weeks after the second boost (post-boost).
Figure 12:
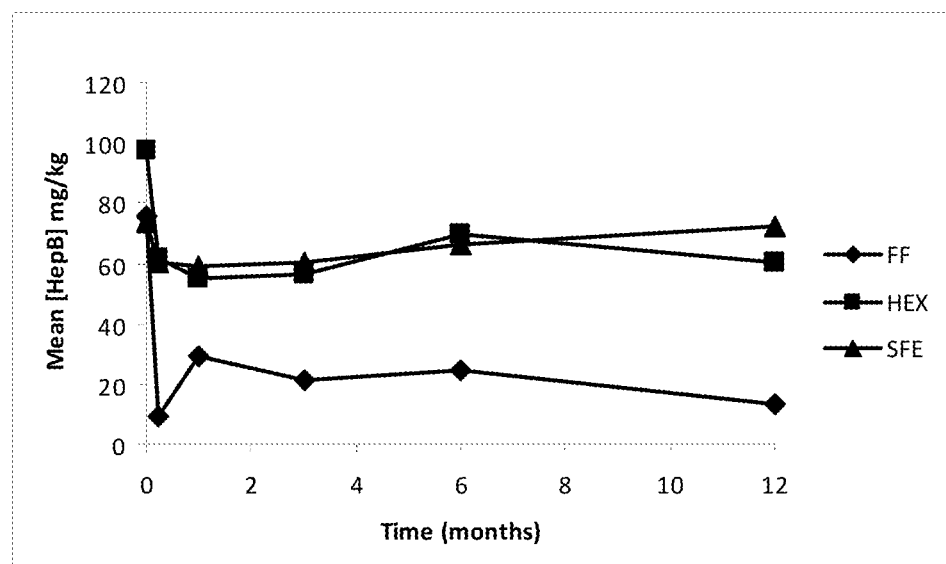
FIG. 12 is a graph showing HBsAg stability at 55° C. over 12 months. FF refers to full fat; HEX refers to hexane-treated; and SFE refers to SFE treated. Whole seed from lines CC100029)1, )2, and )3 were mixed, ground, and placed in a 55° C. incubator for up to 12 months.

Another metric for detecting serum antibody responses, mIU/mL, was assessed using the ETI-AB-AUK PLUS Dia-Sorin kit. Post-boost titers were highest for SFE wafer-fed and RECOMBIVAX® boosted mice, while full fat and hexane-treated wafers produced smaller increases and lower overall titers. As expected, the control germ wafers produced no response in mice and resulted in a decrease in titer after boosting. Although all the mice presented in FIG. 11 were injected with 0.5 µg RECOMBIVAX® on day 0, there was substantial variability in the pre-boost titers across all treatments.

Discussion

Both hexane and SFE treatment preferentially extract non-polar lipids such as triglycerides, yet they differ in their extraction of phospholipids. SFE treatment extracts at least 10 to 100-fold fewer phospholipids than hexane treatment and concentrates phospholipids in the solid fraction. Since HBsAg is an integral membrane protein, is known to be associated with phospholipids in human serum, and has improved immunogenicity when incorporated into lipid micelles, the phospholipid content in the wafers is here believed to alter the immunogenic and structural properties of the protein. This hypothesis is supported by protein blot analysis of the three germ treatments, in which SFE-treated germ showed preferential dimer formation whereas hexane-treated and full fat germ showed preferential monomer formation. This difference would explain differences observed in the immunologic response in the subsequent mouse trials. It would also explain the discrepancy between relative germ concentrations of HBsAg as determined by ELISA versus protein blot. Higher concentration in hexane-treated material seen by ELISA may result from an HBsAg molecule that is more fully exposed for lack of phospholipid components and an enrichment of monomeric subunits, therefore leading to increased binding of the polyclonal antibody used for detection.

Differences between the germ treatments were most striking in the fecal secretory IgA response to oral boosting. SFE-treated wafers produced the strongest response, while hexane-treated wafers produced the weakest response to the orally-administered HBsAg. Interestingly, no response was detected from the RECOMBIVAX®-injected boost, suggesting that mucosal immunologic responses against HBsAg are largely induced by antigen delivered via mucosal routes. This may have important implications for protection against pathogens that primarily invade mucosal surfaces. These data reflect that oral boosting can provide a more balanced systemic/mucosal response than injection alone.

Increased mucosal antibody titers for orally boosted mice were also evident in saliva, albeit at low titers, and were absent in RECOMBIVAX®-injected and control mice. Smaller increases in saliva titers may be explained by the high turnover of fluid in the oral cavity, or perhaps a suboptimal response due to a timepoint collection with a non-maximal titer. Because saliva collection is physically demanding for the mice, a more thorough characterization of the salivary IgA response over time will need to be conducted in human volunteers or a larger model organism.

Another aim of the study was to compare the systemic response for injected boosting and oral boosting regimes. In serum, oral boosting with SFE material was comparable to injected boosting, as assessed by IgG and IgA pre-boost normalized titers. The fold increase in IgG titer from SFE boosting was lower than RECOMBIVAX® boosting, but not statistically different. Serum IgA seemed to show a much greater response in mice fed SFE wafers, with titers more than 3-fold above pre-boost levels, while the RECOMBIVAX® injections resulted in a 2-fold increase above pre-boost levels. It is not clear whether these fold-changes were influenced by pre-boost titers, since SFE-treated pre-boost titers were two-fold lower than RECOMBIVAX® pre-boost titers. Nonetheless, it can be argued that the boosting effect is at least comparable in both treatments, as final post-boost titers were similar.

Serum titers were also assessed by assaying mIU/mL of total Ig anti-HBsAg antibody. As seen with the serum IgA titers, mouse treatments showed very different pre-boost titers, despite all mice receiving equivalent primary injections at the initiation of the study. When comparing SFE and RECOMBIVAX® treatments, there was no statistical difference when analyzing either the total mIU/mL titers in the post-boost (terminal) bleed, or the change in titer from pre- to post-boost bleeds. In addition, terminal bleed titers were lower in hexane-treated and full fat fed mice and significantly different than RECOMBIVAX®-boosted mice. SFE treatment, therefore, seems to be the preferred oral boosting option of the three wafer treatments.

Viability of a 2-dose oral boosting regime was also confirmed. This study clearly shows that two oral doses can induce a robust immune response, and demonstrates that oral boosting is a viable alternative to parenteral boosting. Additional mouse studies confirmed the above.

These data establish the viability of an oral vaccine for hepatitis B in the absence of an adjuvant. They indicate that serum titers in mice boosted orally with SFE material or parenterally with RECOMBIVAX® injection are comparable, and that SFE material is far more effective than RECOMBIVAX® for inducing a mucosal response. Hexane-treated and full fat wafers also induced immunologic responses, but with reduced efficacy relative to the SFE-treated wafers and the RECOMBIVAX® injected booster doses.

EXAMPLE 7

Increasing stability of membrane-bound proteins is another challenge faced by the industry. Even if seed may be stored over time, the stability of the membrane-bound protein may not be retained.

For optimum results, it is important to retain integrity of membrane-bound proteins, such as HBsAg under a range of ambient temperatures over extended periods of time to eliminate the need for the cold chain. Corn kernels are known to keep recombinant proteins stable for years at ambient temperatures but it was not known the effect grinding and formulation would have on protein stability. Tests showed ground seed did lose some activity at ambient temperatures over one month while defatted germ flour appeared much more stable (Hayden, et al. (2012) "Production of highly concentrated, heat-stable hepatitis B surface antigen in maize" *Plant Biotechnology Journal* 10, 979-984). To test this more extensively, full fat or defatted ground seed samples were subjected to different temperature regimes over a one-year period. Grain was ground and stored at various temperatures or defatted prior to storage by SFE. Maize meal was extracted in buffer, HBsAg measured by ELISA and compared to the amount of HBsAg at time 0. HBsAg showed no loss of activity for one year at 55° C. in SFE-treated material while full-fat seed material showed considerable loss (see FIG. 12). Conceivably, defatted germ could be transported and administered in the hottest of climates, which rarely rise above 50° C. (122° F.), without adversely affecting its immunogenicity. Verification of maize-based HBsAg to elicit an immune response in mice after long-term storage is further confirmed.

Several ways to formulate the vaccine candidate, starting with defatted germ flour, were examined. Such flour can then be formed into a readily edible form or food product, using any convenient method, such as combining with a liquid to form a dough and shaping the dough. Any of a variety of forms could be used, such as a biscuit, cookie, wafer, for example. The most promising method was to form small wafers that can be easily consumed such as those described above, for example. In preparing these wafers, it was found that incubation for 2 hours at various temperatures after the addition of water reduced the HBsAg levels considerably. It was empirically determined that mixing 2.5 g defatted germ with about 0.65 g sugar, adding about 0.35-0.75 g water so as to form a wafer in a plastic mold, and drying them in a vacuum oven until >90% of the added water was removed provided a convenient method to deliver a precise dosage in a stable palatable form.

EXAMPLE 8

Mouse trials are conducted using plant material expressing membrane-bound proteins, including HIVgp120 segment of the env gene (GenBank accession U63632) in which codons were changed to reflect optimal codon usage in corn and to eliminate any potential message destabilizing sequences as is described at US Patent Application 20040040061, incorporated herein by reference in its entirety.

What is claimed is:

1. A method of increasing an immune response in an animal to a plant-produced hepatitis B membrane-bound polypeptide, the method comprising,
   a) introducing a hepatitis B surface antigen (HBsAg) membrane-bound polypeptide in a plant, plant part, plant tissue or plant cell;
   b) extracting lipids from germ or seed or both by a process that extract more nonpolar lipids than phospholipids and removes a lower amount of phospholipids than hexane extraction to produce a plant composition comprising said germ or seed or both, wherein said germ or seed or both comprises said HBsAg, and wherein said process comprises supercritical fluid extraction;

c) administering said plant composition having said lipids extracted comprising said membrane-bound polypeptide to an animal; and producing an increased immune response in said animal to said HBsAg membrane-bound polypeptide compared to immune response when administering to said animal said plant-produced membrane-bound polypeptide wherein lipids are extracted from a plant, plant part, plant tissue or collection of plant cells comprising said hepatitis B membrane-bound polypeptide by a process that does not extract more nonpolar lipids than phospholipids and a lower amount of phospholipids than hexane extraction.

2. The method of claim 1, wherein said membrane-bound polypeptide is administered to said animal and increases said immune response by at least 25%.

3. The method of claim 1, wherein said plant composition is orally administered to said animal.

4. The method of claim 1, wherein said plant composition comprises flour and further comprising orally administering said flour to said animal.

5. The method of claim 3, wherein said membrane-bound polypeptide is administered to said animal and said immune response comprises production of mucosal antibodies, production of serum antibodies or both.

6. The method of claim 3, wherein said oral administration is a booster administration.

7. The method of claim 1, wherein said process removes at least two fold lower amount of phospholipids than hexane extraction.

8. The method of claim 1, wherein said process removes at least ten fold lower amount of phospholipids than hexane extraction.

9. The method of claim 1, wherein said plant, plant part, plant tissue or plant cell comprises maize.

10. The method of claim 1, wherein said plant, plant part, plant tissue or plant cell comprises a monocotyledonous plant, plant part, plant tissue or plant cell.

11. The method of claim 1, further comprising after extracting said lipids, determining if said membrane-bound polypeptide has a higher amount of said membrane-bound polypeptide in a preferred formation than in non-preferred formation; and selecting said membrane-bound polypeptide where there is a higher amount of membrane-bound polypeptide in said preferred formation.

12. The method of claim 1, wherein and said plant, plant part, plant tissue or plant cell comprises maize.

13. A method of increasing an immune response of a plant-produced membrane-bound polypeptide, said method comprising, a) introducing a hepatitis B surface antigen (HBsAg) membrane-bound polypeptide in a plant, plant part, plant tissue or plant cell;

b) reducing lipid content in germ or seed or both by supercritical fluid extraction to produce a plant composition comprising said germ or seed or both, wherein said germ or seed or both comprises said HBsAg; and c) providing said plant composition comprising said HBsAg membrane-bound polypeptide in an orally acceptable composition such that said polypeptide produces an increased immune response when administered to an animal, compared to said membrane-bound polypeptide produced in a plant composition in which lipid content is reduced by hexane extraction.

\* \* \* \* \*

SEQUENCE LISTING

```
<160> NUMBER OF SEQ ID NOS: 12

<210> SEQ ID NO 1
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atggccaaca agcacctgag cctctccctc ttcctcgtgc tcctcggcct ctccgcctcc      60
ctcgccagcg gcgagtccac cacctccggc ttcctcggcc cgctcctcgt gctccaggcc     120
ggcttctccc tcctcacccg catcctcacc atcccgcagt ccctcgactc ctggtggacc     180
tccctcaact tcctcggcgg cgccccgacc tgcccggggc agaacctcca gtccccgacc     240
tccaaccact ccccgacctc ctgccccgcc acctgccgg gctaccgctg gatgtgcctc      300
cgccgcttca tcatcttcct ctttcatcctc ctgctctgcc tcatcttcct cctcgtgctc     360
gtggactacc agggcatgct cccggtgtgc ccgctcctcc cgggcacctc cacgacctcc     420
accggcccgt gcaagacctg caccatcccg gcccagggca cctccatgtt cccgtcctgc     480
tgctgcacca agccgtccga cggcaactgc gcctgcatcc cgatcccgtc ctcctgggcc     540
ttcgcccgct tcctctggga gtgggcctcc gtgcgcttct cctggctctc cctcctcgtg     600
ccgttcgtgc agtggttcgt gggcctctcc ccgaccgtgt ggctctccgt gatctggatg     660
atgtggtact ggggcccgtc cctctacaac atcctctccc cgttcctccc gctcctcccg     720
atcttcttct gcctctgggt gtacatctga                                      750

<210> SEQ ID NO 2
<211> LENGTH: 675
<212> TYPE: DNA
<213> ORGANISM: Hepatitis B virus

<400> SEQUENCE: 2
gagtccacca cctccggctt cctcggcccg ctcctcgtgc tccaggccgg cttctccctc      60
ctcacccgca tcctcaccat cccgcagtcc ctcgactcct ggtggacctc cctcaacttc     120
ctcggcggcg ccccgacctg cccgggccag aacctccagt ccccgacctc caaccactcc     180
ccgacctcct gccgcccac ctgcccgggc taccgctgga tgtgcctccg ccgcttcatc      240
atcttcctct catcctcct gctctgcctc atcttcctcc tcgtgctcgt ggactaccag      300
ggcatgctcc cggtgtgccc gctcctcccg ggcacctcca cgacctccac cggcccgtgc     360
```

```
aagacctgca ccatcccggc ccagggcacc tccatgttcc cgtcctgctg ctgcaccaag    420
ccgtccgacg gcaactgcgc ctgcatcccg atcccgtcct cctgggcctt cgcccgcttc    480
ctctgggagt gggcctccgt gcgcttctcc tggctctccc tcctcgtgcc gttcgtgcag    540
tggttcgtgg gcctctcccc gaccgtgtgg ctctccgtga tctggatgat gtggtactgg    600
ggcccgtccc tctacaacat cctctccccg ttcctcccgc tcctcccgat cttcttctgc    660
ctctgggtgt acatc                                                     675

<210> SEQ ID NO 3
<211> LENGTH: 72
<212> TYPE: DNA
<213> ORGANISM: Hordeum vulgare

<400> SEQUENCE: 3
atggccaaca agcacctgag cctctcctc ttcctcgtgc tcctcggcct ctccgcctcc     60
ctcgccagcg gc                                                        72

<210> SEQ ID NO 4
<211> LENGTH: 1401
<212> TYPE: DNA
<213> ORGANISM: Zea mays

<400> SEQUENCE: 4
aagcttgccg agtgccatcc ttggacactc gataaagtat atttatttt ttttattttg      60 ccaaccaaac tttttgtggt atgttcctac actatgtaga tctacatgta ccattttggc    120
acaattacat atttacaaaa atgttttcta taaatattag atttagttcg tttatttgaa    180
tttcttcgga aaattcacat ttaaactgca agtcactcga acatggaaaa accgtgcatg    240
caaaataaat gatatgcatg ttatctagca caagttacga ccgatttcag aagcagacca    300
gaatcttcaa gcaccatgct cactaaacat gaccgtgaac ttgttatcta gttgtttaaa    360
aattgtataa aacacaaata aagtcagaaa ttaatgaaac ttgtccacat gtcatgatat    420
catatataga ggttgtgata aaaatttgat aatgtttcgg taaagttgtg acgtactatg    480
tgtagaaacc taagtgacct acacataaaa tcatagagtt tcaatgtagt tcactcgaca    540
aagactttgt caagtgtccg ataaaaagta ctcgacaaag aagccgttgt cgatgtactg    600
ttcgtcgaga tctctttgtc gagtgtcaca ctaggcaaag tctttacgga gtgttttca    660 ggctttgaca ctcggcaaag cgctcgattc cagtagtgac agtaatttgc atcaaaaata    720
gctgagagat ttaggccccg tttcaatctc acgggataaa gtttagcttc ctgctaaact    780
ttagctatat gaattgaagt gctaaagttt agtttcaatt accaccatta gctctcctgt    840
ttagattaca aatggctaaa agtagctaaa aaatagctgc taaagtttat ctcgcgagat    900
tgaaacaggg ccttaaaatg agtcaactaa tagaccaact aattattagc tattagtcgt    960
tagcttcttt aatctaagct aaaaccaact aatagcttat ttgttgaatt acaattagct   1020
caacggaatt ctctgttttt ctaaaaaaaa actgcccctc tcttacagca aattgtccgc   1080
tgcccgtcgt ccagatacaa tgaacgtacc tagtaggaac tcttttacac gctcggtcgc   1140
tcgccgcgga tcggagtccc cggaacacga caccactgtg gaacacgaca aagtctgctc   1200
agaggcggcc acaccctggc gtgcaccgag ccggagcccg ataagcacg gtaaggagag    1260 tacgcggga cgtggcgacc cgtgtgtctg ctgccacgca gccttcctcc acgtagccgc   1320
gcggccgcgc cacgtaccag ggcccggcgc tggtataaat gcgcgccacc tccgctttag   1380
```

```
ttctgcatac agccaaccca a                                            1401

<210> SEQ ID NO 5
<211> LENGTH: 1386
<212> TYPE: DNA
<213> ORGANISM: Zea mays

<400> SEQUENCE: 5
aagcttgccg agtgccatcc ttggacactc gataaagtat attttatttt ttttattttg    60
ccaaccaaac tttttgtggt atgttcctac actatgtaga tctacatgta ccattttggc   120
acaattacat atttcaaaaa atgttttcta taaatattag atttagttcg tttatttgaa   180
tttcttcgga aaattcacat ttaaactgca agtcactcga acatggaaaa accgtgcatg   240
caaaataaat gatatgcatg ttatctagca caagttacga ccgatttcag aagcagacca   300
gaatcttcaa gcaccatgct cactaaacat gaccgtgaac ttgttatcta gttgtttaaa   360
aattgtataa aacacaaata aagtcagaaa ttaatgaaac ttgtccacat gtcatgatat   420
catatataga ggttgtgata aaaatttgat aatgtttcgg taaagttgtg acgtactatg   480
tgtagaaacc taagtgacct acacataaaa tcatagagtt tcaatgtagt tcactcgaca   540
aagactttgt caagtgtccg ataaaaagta ctcgacaaag aagccgttgt cgatgtactg   600
ttcgtcgaga tctctttgtc gagtgtcaca ctaggcaaag tctttacgga gtgtttttca   660
ggctttgaca ctcggcaaag cgctcgattc cagtagtgac agtaatttgc atcaaaaata   720
gctgagagat ttaggccccg tttcaatctc acgggataaa gtttagcttc ctgctaaact   780
ttagctatat gaattgaagt gctaaagttt agtttcaatt accaccatta gctctcctgt   840
ttagattaca aatggctaaa agtagctaaa aaatagctgc taaagtttat ctcgcgagat   900
tgaaacaggg cctaaaatg agtcaactaa tagaccaact aattattagc tattagtcgt    960
tagcttcttt aatctaagct aaaaccaact aatagcttat tgttgaatt acaattagct   1020 caacggaatt ctctgttttt ctaaaaaaaa actgccccctc tcttacagca aattgtccgc   1080
tgcccgtcgt ccagatacaa tgaacgtacc tagtaggaac tcttttacac gctcggtcgc   1140
tcgccgcgga tcggagtccc cggaacacga caccactgtg gaacacgaca aagtctgctc   1200
agaggcggcc acaccctggc gtgcaccgag ccggagcccg gataagcacg gtaaggagag   1260
tacggcggga cgtggcgacc cgtgtgtctg ctgccacgca gccttcctcc acgtagccgc   1320
gcggccgcgc cacgtaccag ggcccggcgc tggtataaat gcgcgccacc tccgctttag   1380
ttctgc                                                             1386

<210> SEQ ID NO 6
<211> LENGTH: 15
<212> TYPE: DNA
<213> ORGANISM: Zea mays

<400> SEQUENCE: 6
atacagccaa cccaa                                                     15

<210> SEQ ID NO 7
<211> LENGTH: 3006
<212> TYPE: DNA
<213> ORGANISM: Zea mays

<400> SEQUENCE: 7
cggtatgaat ttggaaacaa attcagtact tttaaaaaaa tttgttgtag ggagcaaata    60
atacataaaa taatttatgc attatttat tttttatttg taataatatg cttgaaacga   120
```

```
taattcagta tgcatgttgt gccagtgtac tacacgggcg gggggagggg attgagtggg    180
ccagcgcggt gcgtagggta gatgggctga aattgataac tcaagtccga ctaggttctc    240
tttttatttc ccttcctttt ctattttcct ttcttttaat tttcatgctt tcaaactaaa    300
ttcaaattcg agttttgaat ttcagcttct aaattgtaca ctaaaattat atgataaggt    360 aaccccctact attactttta atttttttat tctaccccat attgtttact taggggagaa    420
taattgactt aatcacattc ttcctaggtt tcaattctca atctttcaaa tccacatttt    480
tagatttcta ttttgaattt aaataccagt ttggatttag agttcaattt caaaatacac    540
aaccaaaata ccagcatgaa tgcaaatata ttttatgttt atgtatttac ttttcttttta    600 tactttgctc aaaatagtta ttttcatgta tgaaactcaa taagcaagga actcacgtta    660
ttatataacc taataggaat aatttaggta acataattta tcatcctctt gatttaaaag    720
agatatgcct ccagaataag acacatacta aaataactc taatattgaa taactaaagt    780
cgtacaaatc tctactatta ttcctataaa ataataaaga actagctaca acttcttttaa    840 ggcattattc agggtttaca gcttgagagg catgaaccca tcctgtatac tcctggactt    900
ggaagacaaa atgtcaacca aagtgaaagg ttttcttatg gttgctgcta agagatagat    960
tgaacactag atctctccta agacgtcagg gcatgcgttt agactcctac acatgcgaaa   1020
actgcatctt acagttggaa gaaactatat ctcaccactt cctgcggtgt aactttgccc   1080
aaagatgttg gctcactgtt ggaatcactc cgccccgaac tttggatcta acgcttgcag   1140
tgctacatat tagagcaaga ctaacaatgc cgtggagaat ggaaggtatt ataaccatgt   1200
catggtgcat atggaaatgt cgaaataact ggatattcga aaacataccg ccaacggtgg   1260
cggcctgcaa ggaaatgttc aagactgaaa tgaactacat ctgctaccaa gttaagctcg   1320
agacaggagc taaaagtaga aactggatac aaacactttgt aacatagtga cactcccctt   1380
ttcctttctt ttaccttaga actatacata caatccacat tcaataaaaa tttgtaggta   1440
cgccatacac actaccggaa tccggctctt tgccgagtgt gaggcgcttt gtcgagtgct   1500
ttttgtccag cactcggcaa aaaagtctttt gccatgtgcc gcactcggca aagtcctgct   1560
ctcggtaacg accgcgttta ccgagagcag gactctcgac acagaaatac actcgacaaa   1620
gaaatctttg ccgagagcca aacactcggc gaacggcagc gctcggcaaa gggtcgtcag   1680
ccgccgtcta aagctgacgg tcgttatctt tgtcgagtgc cccctcgtcc gacactcagt   1740
agagcaagct tgccgagtgc catccttgga cactcgataa agtatatttt attttttttt   1800
attttgccaa ccaaactttt tgtggtatgt tcctacacta tgtagatcta catgtaccat   1860
tttggcacaa ttacaaaaat gttttctata actattagat ttagttcgtt tatttgaatt   1920
tcttcggaaa attcacatat gaactgcaag tcactcgaaa catgaaaaac cgtgcatgca   1980
aaataaatga tatgcatgtt atctagcaca agttacgacc gaattcagaa gcagaccaga   2040
atcttcaagc accatgctca ctaaacatga ccgtgaactt gttatccagt tgtttaaaaa   2100
ttgtataaaa cacaaataaa gtcagaaatt aatgaaactt gtccacatgt catgatatca   2160
tatatagagg ttgtgataaa aatttgataa tgtttcggta agttgtgac gtactatgtg   2220 tagaaaccta agtgacctac acataaaatc atagagtttc aatgtagttc actcgacaaa   2280
gactttgtca agtgtccgat aaaaagtatt cagcaaagaa gccgttgtcg atttactgtt   2340
cgtcgagatc tctttgccga gtgtcacact aggcaaagtc tttacggagt ttttttcagg   2400
ctttgacact cggcaaagcg ctcgattcca gtagtgacag taatttgcat caaaaatagc   2460
```

| | |
|---|---|
| cgagagattt aaaatgagtc aactaataga ccaactaatt attagctatt agtcgttagc | 2520 |
| ttctttaatc taagctaaaa ccaactaata gcttatttgt tgaattacaa ttagctcaac | 2580 |
| ggaattctct gttttttcta taaaaaaaag ggaaactgcc cctcatttac agcaaactgt | 2640 |
| ccgctgcctg tcgtccagat acaatgaacg tacctagtag gaactctttt acacgctcgg | 2700 |
| tcgctcgccg cggatcggag tcccaggaac acgacaccac tgtggaacac gacaaagtct | 2760 |
| gctcagaggc ggccacaccc tggcgtgcac cgagccggag cccggataag cacggtaagg | 2820 |
| agagtacggc gggacgtggc gacccgtgtg tctgctgcca cgcagccttc ctccacgtag | 2880 |
| ccgcgcggcc gcgccacgta ccagggcccg gcgctggtat aaatgcgcgc cacctccgct | 2940 |
| ttagttctgc atacagccaa cccaacacac acccgagcat atcacagtga cagacactac | 3000 |
| acgatg | 3006 |

<210> SEQ ID NO 8
<211> LENGTH: 2950
<212> TYPE: DNA
<213> ORGANISM: Zea mays

<400> SEQUENCE: 8

| | |
|---|---|
| cggtatgaat ttggaaacaa attcagtact tttaaaaaaa tttgttgtag ggagcaaata | 60 |
| atacataaaa taatttatgc attattttat tttttatttg taataatatg cttgaaacga | 120 |
| taattcagta tgcatgttgt gccagtgtac tacacgggcg ggggggagggg attgagtggg | 180 |
| ccagcgcggt gcgtagggta gatgggctga aattgataac tcaagtccga ctaggttctc | 240 |
| ttttatttc ccttcctttt ctattttcct ttcttttaat tttcatgctt tcaaactaaa | 300 |
| ttcaaattcg agttttgaat ttcagcttct aaattgtaca ctaaaattat atgataaggt | 360 |
| aaccccctact attacttttta attttttttat tctaccccat attgtttact taggggagaa | 420 |
| taattgactt aatcacattc ttcctaggtt tcaattctca atctttcaaa tccacatttt | 480 |
| tagatttcta ttttgaattt aaataccagt ttggatttag agttcaattt caaaatacac | 540 |
| aaccaaaata ccagcatgaa tgcaaatata ttttatgttt atgtatttac ttttcttta | 600 |
| tactttgctc aaaatagtta ttttcatgta tgaaactcaa taagcaagga actcacgtta | 660 |
| ttatataacc taataggaat aatttaggta acataattta tcatcctctt gatttaaaag | 720 |
| agatatgcct ccagaataag acacatacta aaaataactc taatattgaa taactaaagt | 780 |
| cgtacaaatc tctactatta ttcctataaa ataataaaga actagctaca acttctttaa | 840 |
| ggcattattc agggtttaca gcttgagagg catgaaccca tcctgtatac tcctggactt | 900 |
| ggaagacaaa atgtcaacca agtgaaaggg ttttcttatg gttgctgcta agagatagat | 960 |
| tgaacactag atctctccta agacgtcagg gcatgcgttt agactcctac acatgcgaaa | 1020 |
| actgcatctt acagttggaa gaaactatat ctcaccactt cctgcggtgt aactttgccc | 1080 |
| aaagatgttg gctcactgtt ggaatcactc cgccccgaac tttggatcta acgcttgcag | 1140 |
| tgctacatat tagagcaaga ctaacaatgc cgtggagaat ggaaggtatt ataaccatgt | 1200 |
| catggtgcat atggaaatgt cgaaataact ggatattcga aaacataccg ccaacggtgg | 1260 |
| cggcctgcaa ggaaatgttc aagactgaaa tgaactacat ctgctaccaa gttaagctcg | 1320 |
| agacaggagc taaaagtaga aactggatac aacactttgt aacatagtga cactcccctt | 1380 |
| ttcctttctt ttaccttaga actatacata caatccacat tcaataaaaa tttgtaggta | 1440 |
| cgccatacac actaccggaa tccggctctt tgccgagtgt gaggcgcttt gtcgagtgct | 1500 |
| ttttgtccag cactcggcaa aaaagtcttt gccatgtgcc gcactcggca aagtcctgct | 1560 |

```
ctcggtaacg accgcgttta ccgagagcag gactctcgac acagaaatac actcgacaaa    1620
gaaatctttg ccgagagcca acactcggc gaacggcagc gctcggcaaa gggtcgtcag     1680
ccgccgtcta aagctgacgg tcgttatctt tgtcgagtgc ccctcgtcc gacactcagt     1740 agagcaagct tgccgagtgc catccttgga cactcgataa agtatatttt attttttttt    1800
attttgccaa ccaaactttt tgtggtatgt tcctacacta tgtagatcta catgtaccat    1860
tttggcacaa ttacaaaaat gttttctata actattagat ttagttcgtt tatttgaatt    1920
tcttcggaaa attcacatat gaactgcaag tcactcgaaa catgaaaaac cgtgcatgca    1980
aaataaatga tatgcatgtt atctagcaca agttacgacc gaattcagaa gcagaccaga    2040
atcttcaagc accatgctca ctaaacatga ccgtgaactt gttatccagt tgtttaaaaa    2100
ttgtataaaa cacaaataaa gtcagaaatt aatgaaactt gtccacatgt catgatatca    2160
tatatagagg ttgtgataaa aatttgataa tgtttcggta aagttgtgac gtactatgtg    2220
tagaaaccta agtgacctac acataaaatc atagagtttc aatgtagttc actcgacaaa    2280
gactttgtca agtgtccgat aaaaagtatt cagcaaagaa gccgttgtcg atttactgtt    2340
cgtcgagatc tctttgccga gtgtcacact aggcaaagtc tttacggagt gttttttcagg   2400 ctttgacact cggcaaagcg ctcgattcca gtagtgacag taatttgcat caaaaatagc    2460
cgagagattt aaaatgagtc aactaataga ccaactaatt attagctatt agtcgttagc    2520
ttctttaatc taagctaaaa ccaactaata gcttatttgt tgaattacaa ttagctcaac    2580
ggaattctct gttttttcta taaaaaaaag ggaaactgcc cctcatttac agcaaactgt    2640
ccgctgcctg tcgtccagat acaatgaacg tacctagtag gaactctttt acacgctcgg    2700
tcgctcgccg cggatcggag tcccaggaac acgacaccac tgtggaacac gacaaagtct    2760
gctcagaggc ggccacaccc tggcgtgcac cgagccggag cccggataag cacggtaagg    2820
agagtacggc gggacgtggc gacccgtgtg tctgctgcca cgcagccttc ctccacgtag    2880
ccgcgcggcc gcgccacgta ccagggcccg gcgctggtat aaatgcgcgc cacctccgct    2940
ttagttctgc                                                          2950
```

<210> SEQ ID NO 9
<211> LENGTH: 53
<212> TYPE: DNA
<213> ORGANISM: Zea mays

<400> SEQUENCE: 9

```
atacagccaa cccaacacac acccgagcat atcacagtga cagacactac acg           53
```

<210> SEQ ID NO 10
<211> LENGTH: 3006
<212> TYPE: DNA
<213> ORGANISM: Zea mays

<400> SEQUENCE: 10

```
cggtatgaat ttggaaacaa attcagtact tttaaaaaaa tttgttgtag ggagcaaata    60
atacataaaa taatttatgc attatttat tttttatttg taataatatg cttgaaacga     120
taattcagta tgcatgttgt gccagtgtac tacacgggcg gggggagggg attgagtggg    180
ccagcgcggt gcgtagggta gatgggctga aattgataac tcaagtccga ctaggttctc    240
tttttatttc cctccttttt ctattttcct ttcttttaat tttcatgctt tcaaactaaa    300
ttcaaattcg agttttgaat ttcagcttct aaattgtaca ctaaaattat atgataaggt    360
```

```
aaccccctact attactttta atttttttat tctaccccat attgtttact taggggagaa    420
taattgactt aatcacattc ttcctaggtt tcaattctca atctttcaaa tccacatttt    480
tagatttcta ttttgaattt aaataccagt ttggatttag agttcaattt caaaatacac    540
aaccaaaata ccagcatgaa tgcaaatata tttatgttt atgtatttac ttttcttta     600
tactttgctc aaaatagtta ttttcatgta tgaaactcaa taagcaagga actcacgtta    660
ttatataacc taataggaat aatttaggta acataattta tcatcctctt gatttaaaag    720
agatatgcct ccagaataag acacatacta aaaataactc taatattgaa taactaaagt    780
cgtacaaatc tctactatta ttcctataaa ataataaaga actagctaca acttctttaa    840
ggcattattc agggtttaca gcttgagagg catgaaccca tcctgtatac tcctggactt    900
ggaagacaaa atgtcaacca aagtgaaagg ttttcttatg gttgctgcta agagatagat    960
tgaacactag atctctccta agacgtcagg gcatgcgttt agactcctac acatgcgaaa   1020
actgcatctt acagttggaa gaaactatat ctcaccactt cctgcggtgt aactttgccc   1080
aaagatgttg gctcactgtt ggaatcactc cgccccgaac tttggatcta acgcttgcag   1140
tgctacatat tagagcaaga ctaacaatgc cgtggagaat ggaaggtatt ataaccatgt   1200
catggtgcat atggaaatgt cgaaataact ggatattcga aaacataccg ccaacggtgg   1260
cggcctgcaa ggaaatgttc aagactgaaa tgaactacat ctgctaccaa gttaagctcg   1320
agacaggagc taaaagtaga aactggatac aacactttgt aacatagtga cactccccctt  1380
ttcctttctt ttaccttaga actatacata caatccacat tcaataaaaa tttgtaggta   1440
cgccatacac actaccggaa tccggctctt tgccgagtgt gaggcgcttt gtcgagtgct   1500
ttttgtccag cactcggcaa aaaagtcttt gccatgtgcc gcactcggca aagtcctgct   1560
ctcggtaacg accgcgttta ccgagagcag gactctcgac acagaaatac actcgacaaa   1620
gaaatctttg ccgagagcca acactcggc gaacggcagc gctcggcaaa gggtcgtcag    1680
ccgccgtcta aagctgacgg tcgttatctt tgtcgagtgc cccctcgtcc gacactcagt   1740
agagcaagct tgccgagtgc catccttgga cactcgataa agtatatttt attttttttt   1800
attttgccaa ccaaactttt tgtggtatgt tcctacacta tgtagatcta catgtaccat   1860
tttggcacaa ttacaaaaat gttttctata actattagat ttagttcgtt tatttgaatt   1920
tcttcggaaa attcacatat gaactgcaag tcactcgaaa catgaaaaac cgtgcatgca   1980
aaataaatga tatgcatgtt atctagcaca agttacgacc gaattcagaa gcagaccaga   2040
atcttcaagc accatgctca ctaaacatga ccgtgaactt gttatccagt tgtttaaaaa   2100
ttgtataaaa cacaaataaa gtcagaaatt aatgaaactt gtccacatgt catgatatca   2160
tatatagagg ttgtgataaa aatttgataa tgtttcggta aagttgtgac gtactatgtg   2220
tagaaaccta agtgacctac acataaaatc atagagtttc aatgtagttc actcgacaaa   2280
gactttgtca agtgtccgat aaaaagtatt cagcaaagaa gccgttgtcg atttactgtt   2340
cgtcgagatc tctttgccga gtgtcacact aggcaaagtc tttacggagt gttttttcagg  2400
ctttgacact cggcaaagcg ctcgattcca gtagtgacag taatttgcat caaaaatagc   2460
cgagagattt aaaatgagtc aactaataga ccaactaatt attagctatt agtcgttagc   2520
ttctttaatc taagctaaaa ccaactaata gcttatttgt tgaattacaa ttagctcaac   2580
ggaattctct gttttttcta taaaaaaaag ggaaactgcc cctcatttac agcaaactgt   2640
ccgctgcctg tcgtccagat acaatgaacg tacctagtag gaactctttt acacgctcgg   2700
tcgctcgccg cggatcggag tcccaggaac acgacaccac tgtggaacac gacaaagtct   2760
```

```
gctcagaggc ggccacaccc tggcgtgcac cgagccggag cccggataag cacggtaagg    2820
agagtacggc gggacgtggc gacccgtgtg tctgctgcca cgcagccttc ctccacgtag    2880
ccgcgcggcc gcgccacgta ccagggcccg gcgctggtat aaatgcgcgc cacctccgct    2940
ttagttctgc atacagccaa cccaacacac acccgagcat atcacagtga cagacactac    3000
accatg                                                               3006

<210> SEQ ID NO 11
<211> LENGTH: 43
<212> TYPE: DNA
<213> ORGANISM: Zea mays

<400> SEQUENCE: 11
ggatccaaca cacacccgag gatatcacag tcgacactac acc                       43

<210> SEQ ID NO 12
<211> LENGTH: 4
<212> TYPE: PRT
<213> ORGANISM: Unknown
<220> FEATURE:
<223> OTHER INFORMATION: Description of Unknown: "KDEL" motif peptide

<400> SEQUENCE: 12

Lys Asp Glu Leu
1
```